US009617588B2

(12) United States Patent
Kurkela

(10) Patent No.: US 9,617,588 B2
(45) Date of Patent: Apr. 11, 2017

(54) ENZYME MIXTURE

(75) Inventor: Jaakko Kurkela, Espoo (FI)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 215 days.

(21) Appl. No.: 13/252,664

(22) Filed: Oct. 4, 2011

(65) Prior Publication Data

US 2012/0082981 A1   Apr. 5, 2012

Related U.S. Application Data

(60) Provisional application No. 61/389,854, filed on Oct. 5, 2010.

(51) Int. Cl.
*C12N 9/12* (2006.01)
*C12Q 1/68* (2006.01)

(52) U.S. Cl.
CPC ......... *C12Q 1/6848* (2013.01); *C12Q 1/6827* (2013.01); *C12Q 1/6851* (2013.01)

(58) Field of Classification Search
None
See application file for complete search history.

(56) References Cited

U.S. PATENT DOCUMENTS

| | | | |
|---|---|---|---|
| 5,108,892 A | 4/1992 | Burke et al. | |
| 5,436,149 A | 7/1995 | Barnes | |
| 5,466,591 A | 11/1995 | Abramson et al. | |
| 5,541,311 A | 7/1996 | Dahlberg et al. | |
| 6,225,092 B1* | 5/2001 | Kilger et al. | 435/91.2 |
| 6,306,588 B1* | 10/2001 | Solus | C12N 9/1252 435/174 |
| 6,653,077 B1 | 11/2003 | Brenner | |
| 7,052,877 B2 | 5/2006 | Rozzelle et al. | |
| 7,148,049 B2 | 12/2006 | Schoenbrunner et al. | |
| 7,163,790 B2 | 1/2007 | Wang et al. | |
| 7,445,898 B2 | 11/2008 | Li et al. | |
| 7,588,891 B2 | 9/2009 | Prudent et al. | |
| 7,723,103 B2* | 5/2010 | Mead et al. | 435/320.1 |
| 7,960,157 B2 | 6/2011 | Borns | |
| 8,318,469 B2 | 11/2012 | Rozzelle et al. | |
| 2001/0049125 A1 | 12/2001 | Stemmer et al. | |
| 2002/0119461 A1 | 8/2002 | Chatterjee | |
| 2002/0164630 A1 | 11/2002 | Livak et al. | |
| 2004/0115644 A1 | 6/2004 | Dong | |
| 2004/0197800 A1 | 10/2004 | Borns | |
| 2006/0024695 A1 | 2/2006 | Li et al. | |
| 2006/0051749 A1 | 3/2006 | Wang et al. | |
| 2006/0141514 A1* | 6/2006 | Rozzelle et al. | 435/6 |
| 2006/0292578 A1 | 12/2006 | Zheng et al. | |
| 2009/0286251 A1 | 11/2009 | Xu | |

FOREIGN PATENT DOCUMENTS

| | | |
|---|---|---|
| EP | 1 581 630 | 10/2005 |
| EP | 1 456 394 | 8/2008 |
| WO | WO 97/29209 | 8/1997 |
| WO | WO 01/92501 | 12/2001 |
| WO | WO 2010/005919 | 1/2010 |

OTHER PUBLICATIONS

Barnes "The fidelity of Taq polymerase catalyzing PCR is improved by an N-terminal deletion," Gene 1992, 112:29.
Shaw et al., "Oligonucleoside Boranophosphate (borane phosphate)," Methods Mol. Biol. 20: 225-43 (1993).
Twyman et al., "Techniques Patents for SNP Genotyping," Pharmacogenomics, Jan. 2003, vol. 3, No. 3; pp. 67-79.
Whitman et al., "Real-Time Polymerase Chain Reaction Detection Methods," Recent Patents on DNA & Gene Sequences, Jan. 2008, vol. 8, No. 1; pp. 20-26.
Pavlov et al., "Helix-hairpin-helix Motifs Confer Salt Resistance and Processivity on Chimeric DNA Polymerases," Proc. Natl. Acad. Sci USA, Oct. 15, 2002, vol. 99, No. 2; pp. 113510-13515.
Motz et al., "Elucidation of an Archaeal Replication Protein Network to Generate Enhanced PCR Enzymes" J. Biol. Chem., May 3, 2002, vol. 27,7 No. 18; pp. 16179-16188.
Lawyer et al., "High-level Expression, Purification, and Enzymatic Characterization of Full-Length Thermus aquaticus DNA Polymerase and a Truncated Form Deficient in 5' to 3' Exonuclease Activity," Genome Res., May 1993, vol. 2; 275-287.
Kong et al., "Characterization of a DNA Polymerase from the Hyperthermophile Archaea *Thermococcus litoralis*," J. Biol. Chem, Jan. 25, 1993, vol. 268, No. 3; pp. 1965-1975.
Nielsen et al., "Sequence-Selective Recognition of DNA by Strand Displacement with a Thymine-Substituted Polyamide," Science, Dec. 6, 1991, vol. 254; pp. 1497-1500.
International Search Report and Written Opinion of the World Intellectual Property Organization for PCT/IB2011/002709, mailed Mar. 27, 2012.
Huang and Li. Characterization of the 5' to 3' nuclease activity of Thermus aquaticus DNA polymerase on fluorogenic double-stranded probes. Molecular and Cellular Probes vol. 23 (2009), pp. 188-194.
Livak. Allelic discrimination using fluorogenic probes and the 5' nuclease assay. Genetic Analysis, vol. 14 (1999), pp. 143-149.
Solinas, A. et al.: Intramolecular TagMan probes for genetic analysis. Chemical Communications—Chemcom [6015D], Royal Society of Chemistry, GB, No. 19, Oct. 7, 2002, pp. 2272-2273.
Oligonucleotides and Analogues, Chapts. 4, 5, 6, IRL Press, New York (1991).

\* cited by examiner

*Primary Examiner* — Richard Hutson
(74) *Attorney, Agent, or Firm* — McNeill Baur PLLC

(57) ABSTRACT

Polymorphisms are present throughout an organism's genome, and understanding which alleles are present in a particular organism's genome can be advantageous. When probing the identity of these alleles, one must minimize incorrect readings due to inefficiencies in the system. In hydrolysis probe applications, these inefficiencies may be due to over-activity of an exonuclease functionality that excises nucleotides from probes that are only partially, complementary to a region of a target. The present invention provides a mixture that contains a plurality of polymerases including one that has a 5'→3' exonuclease functionality and one that lacks or substantially lacks it, each in a sufficient relative amount and concentration to increase efficiencies of the system.

59 Claims, 11 Drawing Sheets

ENZYME MIXTURE

This application claims priority to U.S. Application Ser. No. 61/389,854 filed Oct. 5, 2010, which is expressly incorporated by reference herein in its entirety.

BACKGROUND

Polymerases are members of a class of template dependent enzymes that can catalyze the growth of a chain of nucleotides. Depending on the configuration of the active site or sites within a polymerase, the enzyme may have a polymerization functionality that imparts the ability to join together two ribonucleotide units, two deoxyribonucleotide units or a ribonucleotide unit and a deoxyribonucleotide unit. By way of example, a DNA dependent DNA polymerase utilizes a DNA template and produces a DNA strand that is complementary to at least a portion of a DNA template. An RNA-dependant DNA polymerase, e.g., a reverse transcriptase, uses an RNA template to produce a DNA strand that is complementary to at least a portion of an RNA template. Examples of known polymerases include DNA polymerase I, DNA polymerase II, DNA polymerase III, DNA polymerase α, DNA polymerase β, DNA polymerase γ, DNA polymerase δ and DNA polymerase ε.

As persons of ordinary skill in the art are aware, when joining two nucleotides together, or adding a nucleotide to a growing chain of nucleotides, polymerases rely on a template strand to determine what should be the next nucleotide in the growing chain. Thus, they read the template strand but write the opposite strand.

By convention, individual nucleotides are described as having 5' and 3' positions, and in a chain the 3' position of one nucleotide is linked to the 5' position of the next nucleotide. Because each nucleotide has a 5' end and a 3' end, each strand of nucleotides is referred to as having a 5' end, which refers to the position at the end of the strand that has a nucleotide with a 5' position that is not bound to another nucleotide, and a 3' end, which refers to the position at the end of the strand that has a nucleotide with a 3' position that is not bound to another nucleotide.

Polymerases grow a chain from the 3' end, and they add the next nucleotide by joining the 5' end of the nucleotide to be added to the 3' end of the chain. Thus, polymerases are said to write in a 5'→3' direction.

When adding nucleotides to a growing chain, polymerases prefer to obey the Watson-Crick rules for base pairing, i.e., when a DNA or RNA polymerase is used and there is a C on a template strand, preferably on the growing strand it should incorporate a G; when a DNA or RNA polymerase is used and there is a G on a template strand, on the growing strand it should incorporate a C; when a DNA polymerase is used and there is an A on a template strand, on the growing strand it should incorporate a T; when a DNA polymerase is used and there is a T or a U on a template strand, on the growing strand it should incorporate an A; when an RNA polymerase is used and there is an A on a template strand, on the growing strand it should incorporate a U; and when an RNA polymerase is used and there is a U or a T on a template strand, on the growing strand it should incorporate an A.

Polymerases may have multiple functionalities. For example, certain polymerases also have an exonuclease functionality in addition to a polymerizing functionality. An exonuclease functionality refers to the ability of the polymerase to remove nucleotides. Some polymerases may have either a 3'→5' exonuclease functionality, or a 5'→3' exonuclease functionality, or both functionalities, or neither functionality. The phrase "exonuclease functionality" refers to the ability to remove a nucleotide that the enzyme, depending on its identity and the reaction conditions, determines is located in a place that it should not be, which may, for example, be due to there being a mismatch or a modification to the nucleotide, or a nucleotide being ahead of a growing chain and incompatible with the current chain growth. Thus, if the exonuclease is a 5'→3' exonuclease, it removes nucleotides that are in front of it as it moves in the 3' direction and grows a chain of nucleotides. A polymerase with 5'→3' exonuclease activity displaces a few bases from the 5' end and cleaves one or a few bases from the displaced end. Thus, the 5'→3' activity is also an endonuclease. An example of a DNA polymerase is Finnzymes' Native thermostable DyNAzyme™ I DNA Polymerase. That enzyme is isolated and purified from *Thermus brockianus*, which is a Finnzymes' proprietary strain. It contains 5'→3' exonuclease functionality. In contrast, 3'→5' exonuclease functionality refers to the ability to remove nucleotides from the 3' terminus of a nucleic acid.

Polymerases are well known tools for use in applications that seek to sequence the content of the genome or sections of it. Polymerases with altered functionalities have been used in DNA sequencing applications. One example is a method for sequencing DNA using a mixture of polymerases, one polymerase with a reduced ability to incorporate dideoxynucleotides (ddNTPs) into a synthesized DNA strand, the other polymerase allowing incorporation of ddNTPs into the synthesized strand, due to a Tabor-Richardson mutation in which tyrosine replaces phenylalanine in the polymerase crevice. During polymerization of the DNA being synthesized, the mutation is responsible for discriminating between incorporation of either deoxynucleotides or dideoxynucleotides. The result of using this polymerase mixture is an increased statistical probability that chain termination occurs due to dideoxynucleotide incorporation into the DNA being synthesized, which permits amplification and sequencing reactions to be performed with fewer manipulations (U.S. Pat. No. 6,225,092). Another example is a mixtures of polymerases used in DNA sequencing, DNA labeling, DNA amplification, cDNA synthesis reactions, or analyzing and/or typing polymorphic DNA fragments. The polymerase mixture contains a polymerase having 5'→3' exonuclease activity (exo+) and a polymerase having reduced 5'→3' exonuclease activity (exo−), where the presence of the exo− polymerase enhances PCR performance by increasing the amount of product produced (U.S. Patent Application Publication No. 20060292578). Because these methods to analyze and/or type polymorphic DNA fragments compare the size or the sequence of the resulting amplified fragments, enhanced PCR performance facilitate such size comparisons or the ability to sequence an amplified fragment from each individual. Another example is use of blends of chimeric and non-chimeric thermostable DNA polymerases in DNA sequencing, where the blend of chimeric and non-chimeric polymerases allows PCR reactions with shorter extension times that facilitate PCR amplification of genomic DNA templates and improve efficacy of long PCR.

Polymerases can be used in combination with a hydrolysis probe assay which may, e.g., rely on Taqman® chemistry. In these hydrolysis probe assays, the polymerase with 5'→3' exonuclease activity, e.g., Taq polymerase from *Thermus aquaticus*, can catalyze the growth of a chain of oligonucleotides and also degrade from the 5' direction, a hybridized non-extendible DNA probe during the PCR extension step.

The probe that is degraded is designed to hybridize to a region within the amplicon and is dually labeled with a reporter dye and a quencher dye. The close proximity of the quencher dye to the reporter dye suppresses the fluorescence of the reporter dye. During amplification and in the presence of non-terminating nucleotides and primers that span the probe site, the polymerase will grow a strand until it gets to the probe. Next it will excise the probe from the 5' end, thereby degrading it. After the exonuclease activity of the polymerase degrades the probe, the reporter dye fluorescence increases because the reporter dye is not quenched by the quencher dye. Fluorescence increase is proportional to the number of probes cleaved, and thus is also proportional to the amount of template present.

Some variants of hydrolysis probe assays rely on a 3'→5' exonuclease activity, e.g. proofreading activity, to generate a signal. For example, U.S. Pat. No. 7,163,790 describes an "error-correcting assay" using an oligonucleotide probe labeled on the 3' nucleotide, and a polymerase having 3'→5' exonuclease activity, referred to as a "error-correcting polymerase". In this error correcting assay, if there is a match between the labeled 3' nucleotide of the probe and the target nucleic acid, e.g., if the 3' nucleotide anneals to the target nucleic acid, the labeled 3' nucleotide is not accessible to the 3'→5' exonuclease activity of the error correcting polymerase. If, however, there is a mismatch between the labeled 3' nucleotide and the target nucleic acid, the labeled 3' nucleotide is accessible to the 3'→5' exonuclease activity of the error correcting polymerase and is cleaved. Cleavage of the labeled 3' nucleotide is then detected, e.g., by a decrease in fluorescence polarization. This error correction method relying on 3' labeling and 3'→5' exonuclease activity has been expanded to include methods for quantifying nucleic acid amplification using unlabeled primers (U.S. Patent Application Publication No. 20060024695). U.S. Pat. No. 7,445,898 describes use of polymerases and/or enzymes having 3'→5' exonuclease activity, where the ratio of double stranded (ds) to single stranded (ss) 3'→5' exonuclease activity is optimized to result in greater label cleavage from the 3' end of a labeled probe, and therefore greater signal.

One variation of hydrolysis probe assay chemistry is an assay for allelic discrimination. For example, humans have two copies of the genome in each cell. These copies are not exactly the same and have many types of sequence variations. One of these variation types is the single nucleotide polymorphism (SNP), in which the nucleotide base sequence has a single nucleotide difference from the normal type. When both copies of the genome sequence are the same for a certain region, the individual may be referred to as homozygous. When the copies are different in this region, the individual may be referred to as heterozygous. When both copies represent the normal type, the individual may be referred to as being a homozygous wild type. When both copies represent the same difference from the normal type, the individual may be referred to as being a homozygous mutant. For typical variations in the genome there are three different genotypes: homozygous wild type, homozygous mutant, and heterozygous. Hydrolysis assays can be used for discriminating these types. The typical discrimination assay contains two primers that define the region that contains the variation of interest to be amplified, and two probes, each specific for one type of sequence variant and labeled with different reporter fluorophores. In the homozygous sample, only one type of the probe hybridizes and is cleaved to produce a signal. In the heterozygous sample, both probes bind and produce a signal. The sample genotype is determined from the fluorescence data by comparing the intensity changes of each probe before and after the PCR reaction or in each cycle in real time qPCR.

Unfortunately, in these applications there can be unacceptably high levels of incorrect or ambiguous results. Under common conditions, there may be quick and efficient cleavage of any bound probe, which includes a probe with a mismatch that binds transiently to the target sequence and thus is present long enough for the exonuclease activity to occur. This false positive can lead to fluorescence increases even when cleavage should not have occurred, thereby leading to poor allelic discrimination due to a high mismatch signal. This in turn may cause an incorrect sequence or allele to be inferred, or there may be an unacceptable level of ambiguity. These undesirable results are unfortunately too common when probes differ by a few nucleotides or only one nucleotide, as is the case with single nucleotide polymorphisms. Thus, there is a need to improve hydrolysis probe assay systems used for allelic discrimination and applications in which the mixtures are used.

SUMMARY OF THE INVENTION

The inventive compositions and methods solves these problems in hydrolysis probe assays for allelic discrimination. A mixture of at least two polymerases is used: a first polymerase has 5'→3' exonuclease activity (exo+), and a second polymerase lacks or substantially lacks 5'→3' exonuclease activity (exo−) and to the extent the second polymerase has 5'→3' exonuclease activity the ratio of the first and second polymerases may be further modified to compensate for the increase in 5'→3' exonuclease activity in the mixture. By optimizing the ratio of the exo+ and exo− polymerases, where the exo− polymerase is the prevalent enzyme, the number of false positives was reduced in a hydrolysis probe assay. Without being held to a single theory, the overall abundance of exo− enzyme in the hydrolysis probe assay increases the amount of time a probe must remain annealed to a target sequence in order for the probe to be degraded; this increase in required annealed time decreases the likelihood that a mis-annealed probe will be degraded in the assay. The total amount of polymerase activity in the polymerase mixture is balanced against the 5'→3' exonuclease activity in the polymerase mixture to result in efficient amplification of a target nucleic acid in the hydrolysis probe assay. In one embodiment, at least one, more than one, or all of the polymerases forming the polymerase mixture, and therefore, the polymerase mixture itself, lack or have a reduced 3'→5' exonuclease activity, e.g., proofreading activity, with a reduced activity being less 3'→5' functionality than a wild type polymerase. Without being held to a single theory, the lack or reduction of 3'→5' exonuclease activity, in conjunction with the described amount of 5'→3' exonuclease activity, improves hydrolysis probe assay results by decreasing the likelihood that a mis-annealed probe will be degraded.

The inventive compositions and methods discriminate between matched and mismatched targets, while reducing improper mismatched signals. In one embodiment, a mixture of enzymes is provided comprising: (i) a first enzyme, wherein the first enzyme is a polymerase that has a 5'→3' exonuclease functionality and (ii) a second enzyme, wherein the second enzyme is a polymerase that lacks or substantially lacks a 5'→3' exonuclease functionality, wherein the ratio of the first enzyme to the second enzyme permits allelic discrimination of a polymorphism. In some embodiments, the total amount of polymerase, i.e., the combined amount of first enzyme and second enzyme may, e.g., for example, be between 100 polymerase activity units per milliliter and 500 polymerase activity units per milliliter.

This mixture is particularly useful in hydrolysis probe based genotyping reactions using, e.g., Taqman® probes, that rely on 5' hydrolysis of the probe. The mixture improves allelic discrimination and ameliorates the problems of false positive-results that occur when too much exonuclease is delivered to a reaction.

One embodiment is a composition comprising a first DNA polymerase that has a 5'→3' exonuclease functionality, and a second DNA polymerase that lacks or substantially lacks a 5'→3' exonuclease functionality, at a ratio of the first polymerase to the second polymerase permitting enhanced allelic discrimination of a polymorphism; the combined amount of first and second polymerases in the composition between 100 polymerase activity units per milliliter and 500 polymerase activity units per milliliter, the amount of the first polymerase in the composition from 1% to 50% of the total amount of polymerase and the amount of the second polymerase from 50% to 99% of the total amount of polymerase. In one embodiment the first polymerase is Tbr and possesses a 5'→3' exonuclease functionality, and the second polymerase is Tbr and lacks or substantially lacks a 5'→3' exonuclease functionality. The composition can further comprise at least two hydrolysis probes where each hydrolysis probe comprises at least one of at least one label, a quencher, or a 3' modifying agent (e.g., 3' cap), where the at least one label is a fluorescent dye and the fluorescent dye on each of the hydrolysis probes has distinguishable spectral properties, where the quencher is capable of quenching fluorescence of the fluorescent dye, and where the 3' modification of the hydrolysis probes renders the hydrolysis probes less susceptible to 3'→5' exonuclease degradation. The hydrolysis probes in the composition may anneal to different alleles of a gene, which may be alleles of a polymorphic gene or single nucleotide polymorphisms. In one embodiment, the amount of the first polymerase in the composition is from 1% to 10% of the total amount of polymerase, and the amount of the second polymerase in the composition is from 90% to 90% of the total amount of polymerase. In one embodiment, the amount of the first polymerase in the composition is from 2% to 5% of the total amount of polymerase, and the amount of the second polymerase in the composition is from 95% to 98% of the total amount of polymerase. In one embodiment, the amount of the first polymerase in the composition is from 3% to 4% of the total amount of polymerase. In one embodiment, the first polymerase, the second polymerase, or both the first and the second polymerase in the composition lacks or substantially lacks 3'→5' exonuclease functionality, or has less 3'→5' exonuclease functionality than a wild type.

One embodiment is a method for detecting an allele of a target nucleic acid. In the method a target nucleic acid is combined with a mixture of a first polymerase having a 5'→3' exonuclease functionality and a second polymerase lacking or substantially lacking a 5'→3' exonuclease functionality; at least a first probe capable of annealing to a portion of the target nucleic acid containing a first form of an allele present in the target nucleic acid and comprising a quencher moiety and a first reporter moiety; and a primer complementary to a sequence on the target nucleic acid upstream of the portion of the target nucleic acid complementary to the first probe. Combining is performed under conditions in which the primer can be extended, such that extension of the primer results in degradation of an annealed first probe and separation of the quencher moiety from the first reporter moiety, resulting in a first signal from the first reporter moiety of the first probe. The first signal from the first reporter moiety of the first probe is detected, indicating the presence of the first form of the allele. In one embodiment, the method further combines a second probe capable of annealing to a portion of the target nucleic acid containing a second form of the allele present in the target nucleic acid and comprising a quencher moiety and a second reporter moiety. Degradation of an annealed second probe by extension of the upstream-annealing primer separates the quencher moiety from the second reporter moiety, resulting in a second signal from the second reporter moiety of the second probe. The second signal from the second reporter moiety of the second probe is detected, the second signal distinguishable from the first signal, where detection of the second signal indicates the presence of the second form of the allele. In this embodiment, a comparison of the first signal and the second signal allows for allelic discrimination of the target nucleic acid. In one embodiment, the mixture of the first and second polymerase comprises, based on total amount of polymerase, from 1% to 50% of the first polymerase and from 50% to 99% of the second polymerase, and the combined amount of first polymerase and second polymerase is between 100 polymerase activity units per milliliter and 500 polymerase activity units per milliliter. In one embodiment, the mixture of the first and second polymerase comprises, based on total amount of polymerase, from 1% to 10% of the first polymerase and from 90% to 99% of the second polymerase, and the combined amount of first polymerase and second polymerase is between 100 polymerase activity units per milliliter and 500 polymerase activity units per milliliter. In one embodiment, the first polymerase is Tbr and possesses a 5'→3' exonuclease functionality, and the second polymerase is Tbr and lacks or substantially lacks a 5'→3' exonuclease functionality. In these methods, the first polymerase, the second polymerase, or both the first and the second polymerase can lack or substantially lack a 3'→5' exonuclease functionality, or have less 3'→5' exonuclease functionality than a wild type. In one embodiment, at least one of the first polymerase or the second polymerase is a fusion polymerase, which can comprises a sequence-nonspecific double-stranded nucleic acid binding protein, and which may be a PHUSION™ polymerase. The method may combine a reagent capable of creating a hot start condition with the polymerase mixture.

One embodiment is a kit comprising a polymerase mixture comprising at least a first DNA polymerase that possesses a 5'→3' exonuclease functionality and at least a second DNA polymerase that lacks or substantially lacks a 5'→3' exonuclease functionality, where the amount of the first polymerase in the kit is from 1% to 50% of the amount of total polymerase, and where the amount of the second polymerase in the kit is from 50% to 99% of the amount of total polymerase, and the combined amount of first polymerase and second polymerase in the kit is between 100 polymerase activity units per milliliter and 500 polymerase activity units per milliliter. The kit contains instructions for allelic discrimination of a target nucleic acid using the mixture. In one embodiment, the amount of the first polymerase in the kit is from 1% to 10% of the amount of total polymerase, and the amount of the second polymerase in the kit is from 90% to 99% of the amount of total polymerase. The kit may further comprise at least one probe comprising a quencher moiety and a reporter moiety, with instructions to anneal the probe to a portion of the target nucleic acid. In one embodiment, the first polymerase in the kit is Tbr and possesses a 5'→3' exonuclease functionality, and the second polymerase in the kit is Tbr and lacks a 5'→3' exonuclease functionality.

One embodiment is a method for increasing the fidelity of allelic determination of a target nucleic acid using a dual-labeled probe. The target nucleic acid is contacted with a mixture of a first polymerase having a 5'→3' exonuclease functionality and a second polymerase lacking or substantially lacking a 5'→3' exonuclease functionality, at least one probe, and at least one primer. The probe is capable of annealing to a portion of the target nucleic acid containing the allele, and the probe comprises a quencher moiety and a reporter moiety. The primer is complementary to a sequence of the target nucleic acid upstream of the sequence to which the probe is complementary. Contacting is under conditions in which the primer can be extended such that extension of the primer degrades an annealed probe and separates the quencher moiety from the reporter moiety. A signal from the reporter moiety is detected, indicating the presence of the allele. The method decreases the number of false positive results generated by a mis-annealed probe by balancing the levels of 5'→3' exonuclease and polymerase activities in the mixture. The mixture of the first and second polymerase comprises, based on total amount of polymerase, from 1% to 50% of the first polymerase and from 50% to 99% of the second polymerase, and the combined amount of first polymerase and second polymerase is between 100 polymerase activity units per milliliter and 500 polymerase activity units per milliliter. In one embodiment, the mixture of the first and second polymerase comprises, based on total amount of polymerase, from 1% to 10% of the first polymerase and from 90% to 99% of the second polymerase. In one embodiment, the first polymerase is Tbr and possesses a 5'→3' exonuclease functionality, and the second polymerase is Tbr and lacks or substantially lacks a 5'→3' exonuclease functionality. In one embodiment, at least one of the first polymerase or the second polymerase is a fusion polymerase.

One embodiment is a hydrolysis probe assay method. In the method, a target nucleic acid is combined with a polymerase mixture comprising at least two polymerase enzymes, at least one labeled probe, and at least one primer. The target nucleic acid is amplified using a polymerase chain reaction and the primer. The labeled probe annealed to the target nucleic acid is degraded. Amplification is dependent on a polymerase activity of the polymerase mixture. Degradation is dependent on a 5'→3' exonuclease activity of the polymerase mixture. At least one of the polymerase enzymes of the polymerase mixture possesses a 5'→3' exonuclease activity and at least one of the polymerase enzymes of the polymerase mixture lacks or substantially lacks a 5'→3' exonuclease activity, such that the amount of a product formed in the amplification step is dependent on the total amount of polymerase activity in the mixture, and the amount of probe hydrolyzed in the degradation step is dependent on the ratio of polymerase enzyme(s) possessing 5'→3' exonuclease activity and polymerase enzyme lacking or substantially lacking 5'→3' exonuclease activity in the polymerase mixture.

The invention will be further appreciated with reference to the following figures, description, and examples.

DETAILED DESCRIPTION

Figure 1:
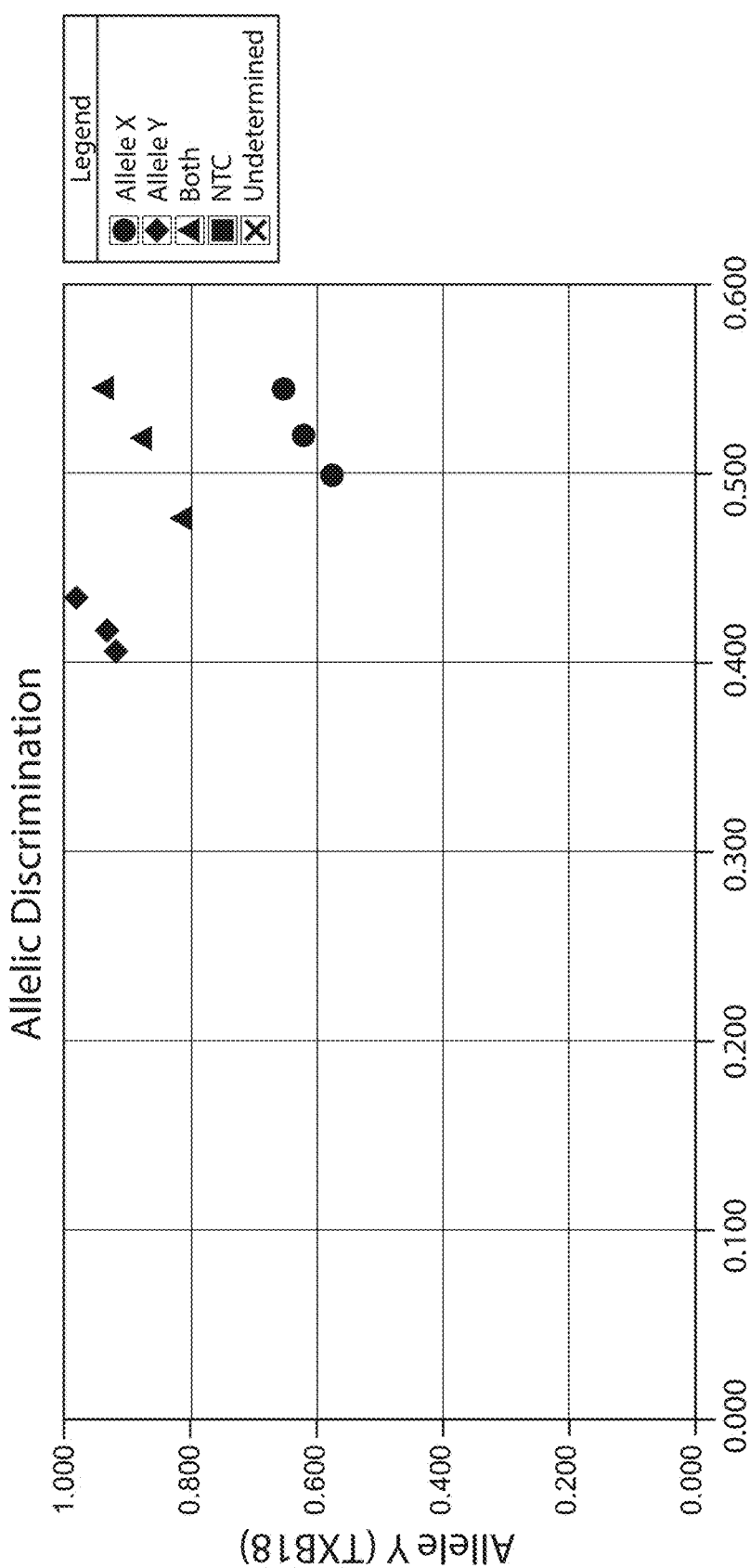
FIG. 1 shows experimental results in which the presence of all three genotypes for TXB18 was measured, and all of the polymerase used had exonuclease activity.

The inventive compositions and kits and use of the inventive methods improved discrimination in hybridization probe analyses between matched and mismatched targets. By designing a novel and non-obvious mixture of enzymes that balanced the presence of polymerase activity and exonuclease activity, the quality and clarity of results obtained from an assay such as a hybridization probe analysis were improved.

According to one embodiment, the mixture of enzymes comprised at least two enzymes. For example, there may be a first enzyme and a second enzyme. Both the first enzyme and the second enzyme may have polymerase activity. They both may be, e.g., DNA polymerases. The term "mixture" refers to a combination of at least two, i.e., two or more, substances that may simultaneously be present. It includes solutions and suspensions. The term "mixture" does not require any uniformity of distribution of the contents, and may exist in solid, liquid or gas form. In some embodiments, the inventive mixtures contain only two polymerases.

The first polymerase enzyme may also have a 5'→3' exonuclease functionality, e.g., it may be a thermostable DNA polymerase including, but not limited to, *Thermus thermophilus* (Tth) DNA polymerase, *Thermus aquaticus* (Taq) DNA polymerase, *hermococcus zilligi* (Tzi) DNA polymerase, *hermotoga neopolitana* (Tne) DNA polymerase, *hermotoga maritima* (Tma) DNA polymerase, *Thermus filiformis* (Tfi) DNA polymerase, Stoffel fragment, Thermoscript, *hermococcus litoralis* (Tli or VENT) DNA polymerase, *yrococcus furiosus* (Pfu) DNA polymerase, DEEPVENT DNA polymerase, *yrococcus woosii* (Pwo) DNA polymerase, *yrococcus* sp KOD2 (KOD) DNA polymerase, *acillus stearothermophilus* (Bst) DNA polymerase, *acillus caldophilus* (Bca) DNA polymerase, *ulfolobus acidocaldarius* (Sac) DNA polymerase, *hermoplasma aci-*

*dophilum* (Tac) DNA polymerase, *Thermus flavus* (Tfl/Tub) DNA polymerase, *Thermus ruber* (Tru) DNA polymerase, *Thermus brockianus* (Tbr) DNA polymerase, *ethanobacterium thermoautotrophicum* (Mth) DNA polymerase, a mycobacterium DNA polymerase (e.g., Mtb, Mlep), and generally Pol I and Pol III type polymerases, and mutants or variants thereof, that have both a polymerase functionality and exonuclease functionality, preferably a 5'→3' exonuclease functionality. In one embodiment, the first polymerase is a Tbr polymerase possessing a 5'→3' exonuclease functionality. In one embodiment, the first polymerase lacks or has a reduced 3'→5' exonuclease functionality. In one embodiment, the first polymerase is DyNAzyme™ II DNA polymerase.

The second polymerase enzyme, however, lacks or substantially lacks a 5'→3' exonuclease functionality. In one embodiment, the second polymerase may also lack, substantially lack, or have a reduced, 3'→5' exonuclease functionality. The first and second enzymes may otherwise be the same except for the lack or substantial lack of 5'→3' exonuclease functionality in the second enzyme. Thus, e.g., both the polymerase enzymes may be DNA polymerase I from the same species, with the second enzyme's 5'→3' exonuclease functionality deactivated or substantially deactivated or reduced due to the substitution, deletion, or addition of one or more amino acids that render the exonuclease functionality inactive or less active (which may e.g., be due to mutation in the DNA that encodes for that polymerase), or the exonuclease site may be blocked through, e.g., a moiety that binds to the site but that is not removed, or binds elsewhere to the enzyme but causes a change in configuration that renders the exonuclease site inactive. In one embodiment, the second polymerase is a Tbr polymerase lacking a 5'→3' exonuclease functionality.

In one embodiment, the first enzyme, the second enzyme, or both are a fusion, e.g., chimeric, protein. For example, one or more protein domains having a desired activity are combined with a DNA polymerase. Fusion of DNA polymerase in frame to the helix-hairpin-helix DNA binding motifs from DNA topoisomerase V increased processivity, salt resistance, and thermostability of the chimeric DNA polymerase (Pavlov et al., 2002, Proc. Natl. Acad. Sci USA, 99:13510). Fusion of the thioredoxin binding domain to T7 DNA polymerase enhanced processivity of the chimeric DNA polymerase in the presence of thioredoxin (WO 97/29209). Fusion of the archaeal PCNA binding domain to Taq DNA polymerase results in a chimeric DNA polymerase that, in the presence of PCNA, enhanced processivity and produced higher yields of PCR amplified DNA (Motz et al., J. Biol. Chem. 2002 May 3; 277 (18); 16179). Fusion of the sequence-non-specific double-stranded nucleic acid binding protein Sso7d or Sac7d from *ulfolobus solfataricus* to a DNA polymerase, such as Pfu or Taq DNA polymerase, greatly increased processivity of these DNA polymerases (WO 01/92501). Domain substitution of all or a portion of a DNA polymerase with the corresponding domain of a different DNA polymerase have been described (U.S. Patent Application Publication No. 2002/0119461).

A fusion polymerase is a protein with at least two heterologous domains. In one embodiment, a first heterologous domain is a sequence-nonspecific double-stranded nucleic acid binding domain, which is joined to a second heterologous domain that is a catalytic nucleic acid modifying domain. The presence of the sequence-nonspecific double-stranded nucleic acid binding domain enhances the processive nature and/or reduces the ability of inhibitors, e.g., fluorescent dyes, impurities present in cell extracts or crude samples, PCR additives, and/or high salt, as described in EP 1 456 394, to inhibit the nucleic acid modifying domain, compared to an identical protein not having a sequence-nonspecific nucleic acid binding domain joined thereto. In one embodiment, the nucleic acid modifying domain can have a polymerase activity, which can be thermally stable, e.g., a *Thermus* polymerase domain. In one embodiment, the sequence-nonspecific nucleic acid binding domain of the fusion polymerase is derived from Sac7d or Sso7d. In one embodiment, the fusion polymerase is a PHUSION® polymerase.

In addition to enhancing inhibitor tolerance of the polymerase mixture, the polymerase mixture may be optimized for other attributes or characteristics of a genotyping assay. For example, the polymerase mixture may be optimized for one or more of the following characteristics: processivity, proofreading, fidelity, DNA binding activity, strand displacement activity, polymerase activity, nucleotide binding and recognition, efficiency, template length amplification capability, GC-rich target amplification efficiency, specificity, thermostability, intrinsic hot start capability, or salt resistance. Although the enhanced inhibitor tolerance is provided by including a PHUSION® polymerase, e.g., a fusion polymerase, in the mixture, mixtures optimized for other attributes, in addition to allelic discrimination, may be derived from mixtures having one, two, or no fusion polymerases. By altering the prevalence of one or more properties of a polymerase in the mixture, the mixture may be formed having certain desired characteristics. For example, polymerization properties are mostly derived from the most abundant polymerase and only minimal properties are provided by the 5'→3' exonuclease containing polymerase. Thus, by mixing different polymerases, properties can be introduced into a genotyping master mix that would not be possible without mixing. Enhanced inhibitor tolerance is one example of the creation of desired properties, in addition to enhanced allelic discrimination, in a polymerase mixture.

In one embodiment, the polymerase mixture comprises a Tbr polymerase with 5'→3' exonuclease activity and a fusion polymerase that lacks 5'→3' exonuclease activity. In one embodiment, the polymerase mixture comprises a Tbr polymerase that lacks 5'→3' exonuclease activity and a fusion polymerase with 5'→3' exonuclease activity. In one embodiment, the polymerase mixture comprises a fusion polymerase that lacks or substantially lacks 5'→3' exonuclease activity and a fusion polymerase with 5'→3' exonuclease activity. In one embodiment, the polymerase mixture comprises a Tbr polymerase that lacks or substantially lacks 5'→3' exonuclease activity and a Tbr polymerase with 5'→3' exonuclease activity. In one embodiment, the polymerase mixture further lacks or substantially lacks or has reduced 3'→5' exonuclease activity. In one embodiment, the fusion polymerase is DyNAmo™ IV and lacks both 5'→3' and 3'→5' exonuclease activities.

By way of a non-limiting example, the polymerase mixture may contain a Tfi polymerase with 5'→3' exonuclease activity and a Tfi polymerase that does not have 5'→3' exonuclease activity. By way of a non-limiting example, the polymerase mixture may contain a Tbr polymerase with 5'→3' exonuclease activity and a Tbr polymerase that does not have 5'→3' exonuclease activity. Various ways, such as mutations and/or deletions, are known in the art for generating polymerases with diminished or eliminated functionalities, such as 5'→3' exonuclease activity and 3'→5' exonuclease activity. For example, Lawyer et al. ("High-level expression, purification, and enzymatic characterization of full-length *Thermus aquaticus* DNA polymerase and a truncated form deficient in 5' to 3' exonuclease activity", Genome Res. 1993 2: 275) describes production of a 5'→3' exonuclease deficient form of Taq polymerase by deletion. Barnes ("The fidelity of Taq polymerase catalyzing PCR is improved by an N-terminal deletion", Gene 1992, 112:29) describes another deletion form of Taq lacking 5'→3' nuclease activity where the first 705 bases from the Taq gene had been deleted. It is known that mutations to a conserved A(V/T)YG domain in thermostable DNA polymerases attenuate or eliminate 5'→3' exonuclease activity (U.S. Pat. No. 5,466,591).

3'→5' exonuclease deficient polymerases have been generated by various known methods. For example, Kong et al. ("Characterization of a DNA Polymerase from the Hyperthermophile Archaea hermococcus litoralis", J. Biol. Chem, 268, 3, pp. 1965 (1993), describes creating a 3'→5' exonuclease deficient Tli DNA polymerase by specific mutations in the putative metal binding domain, and also describes similar mutations shown to eliminate 3'→5' exonuclease activity in E. coli DNA polymerase I, accharomyces cerevisiae DNA polymerase II, and T7 DNA polymerases.

In some embodiments, the first enzyme consists of only one type of polymerase, and the second enzyme consists of only one type of polymerase. In other embodiments, the first enzyme comprises a combination of two or more types of polymerases that share the features of having polymerase and exonuclease functionalities. Similarly, in some embodiments the second enzyme may comprise a plurality of polymerases that have polymerase but not exonuclease functionalities.

In some embodiments, the second enzyme lacks, i.e., is completely devoid of 5'→3' exonuclease functionality. In other embodiments, it substantially lacks, i.e., it has substantially reduced 5'→3' exonuclease activity. In some embodiments, the first and second enzymes are completely devoid of 3'→5' exonuclease functionality. In other embodiments, the first and second enzymes have substantially reduced 3'→5' exonuclease activity. The reduction in functionality may, for example, be due to a mutation that causes the enzyme to have less than 20%, less than 10%, less than 9%, less than 8%, less than 7%, less than 6%, less than 5%, less than 4%, less than 2% or less than 1% of the 5'→3' or 3'→5' exonuclease functionality of the corresponding wild type enzyme. As one of ordinary skill in the art appreciates, 5'→3' and 3'→5' exonuclease functionality (or activity) can be observed on sequencing gels and measured by following the degradation of radio labeled primers.

In some embodiments, less than 98%, or less than 95%, or less than 90%, or less than 85%, or less than 80%, or less than 75%, or less than 70%, or less than 65%, or less than 60%, or less than 55%, or less than 50%, or less than 45%, or less than 40%, or less than 35%, or less than 30%, or less than 25%, or less than 20%, or less than 15%, or less than 10%, or less than 5%, or less than 4%, or less than 3%, or less than 2%, or less than 1% of the total amount of polymerase has 5'→3' exonuclease functionality. The phrase "total amount of polymerase" refers to the combined amount of all polymerase present. For example, when two polymerases are present, it refers to the combined amount of a first polymerase and a second polymerase.

In some embodiments, more than 1%, or more than 2%, or more than 3%, or more than 4%, or more than 5%, or more than 10%, or more than 15%, or more than 20%, or more than 25%, or more than 30%, or more than 35%, or more than 40%, or more than 45%, of the total amount of polymerase contains a 5'→3' exonuclease functionality.

In some embodiments, the amount of polymerase that possesses 5'→3' exonuclease functionality is from 1% to 10%, and the amount of polymerase that lacks or substantially lacks 5'→3' exonuclease functionality is from 90% to 99%. In some embodiments, the amount of polymerase that possesses 5'→3' exonuclease functionality is from 2% to 5%, and the amount of polymerase that lacks or substantially lacks 5'→3' exonuclease functionality is from 95% to 98%. In some embodiments, the amount of polymerase that possesses 5'→3' exonuclease functionality is from 3% to 4%, and the amount of polymerase that lacks or substantially lacks 5'→3' exonuclease functionality is from 96% to 97%.

The amount of total polymerase may be measured in polymerase activity units per milliliter of solution. One unit is defined as the amount of enzyme that will incorporate 10 nmoles of dNTPs into acid-insoluble form at 74° C. in 30 minutes under defined assay conditions. The incubation buffer is 25 mM TAPS-HCl, pH 9.3 (at 25° C.), 50 mM KCl, 2 mM MgCl2, 1 mM (3-mercaptoethanol, 100 µM dCTP, 200 µM each dATP, dGTP, dTTP, 20 µg activated calf thymus DNA and 0.5 µCi [α-32P]dCTP. The amount of incorporated dNTPs is determined by measuring the incorporated radioactivity after trichloroacetic acid precipitation. For example, in some embodiments, there may be between 10 polymerase activity units of the total amount of polymerase per milliliter of solution and 1000 polymerase activity units of the total amount polymerase per milliliter of solution, or between 50 polymerase activity units of the total amount of polymerase per milliliter of solution and 800 polymerase activity units of the total amount of polymerase per milliliter of solution, or between 100 polymerase activity units of the total amount of polymerase per milliliter of solution and 600 polymerase activity units of the total amount of polymerase per milliliter of solution, or between 100 polymerase activity units of the total amount of polymerase per milliliter of solution and 500 polymerase activity units of the total amount of polymerase per milliliter of solution, or between 300 polymerase activity units of the total amount of polymerase per milliliter of solution and 500 polymerase activity units of the total amount of polymerase per milliliter of solution.

In some embodiments, the polymerase mixture may further comprise reagents that prevent enzyme activation until a temperature is reached, i.e., hot start conditions, in an assay or reaction using the polymerase mixture. The hot start technique reduces non-specific amplification and/or primer degradation during the initial set-up stages of a reaction, such as PCR. Hot start may be performed manually by heating the reaction components to the denaturation temperature (e.g., 95° C.) before adding the polymerase. Hot start may also be accomplished by using specialized reagents that inhibit polymerase activity at ambient temperature, such as by binding an antibody or by the presence of covalently bound inhibitors that dissociate only after a high-temperature activation step. For example, the polymerase mixture may further comprise at least one AFFIBODY® molecule, where the AFFIBODY® molecule allows for hot start conditions. In one embodiments, the at least one AFFIBODY® molecule is specific for a Tbr polymerase in the polymerase mixture. In one embodiment, the at least one AFFIBODY® molecule is specific for a portion of a fusion polymerase, for example, a PHUSION® DNA polymerase. The hot start reagents may be specific for the first polymerase, the second polymerase, or both the first and the second polymerase.

The polymerase mixture may also comprise at least one, more than one, or all of a detergent, a buffer, salt, deoxynucleotide phosphates (dNTPs) and dideoxynucleotide triphosphates (ddNTP). These mixtures may be combined with the appropriate PCR primers and solutions, as well as with target sample polynucleotides of interest. Persons of ordinary skill in the art are aware of useful amounts of these compositions for interrogating a genetic sequence.

The polymerase mixture may also comprise one probe, or a plurality of probes, e.g., at least or exactly two probes, three probes, four probes, five probes, six probes, seven probes, eight probes, etc. In addition to probes, the mixture may also contain primers that span the region that is to be interrogated by each probe. These primers may act as starting points for polymerases as they synthesize the growing strands. The probes may each be labeled with a different dye. The probe or probes may contain a 3' modification (e.g., 3' cap or other blocking or protecting functionality) such that the 3' end of the probe is resistant to degradation. In one embodiment, the 3' end of the oligonucleotide probe is rendered resistant or impervious to digestion by including one or more modified internucleotide linkages into the 3' end of the oligonucleotide probe. Minimally, the 3'-terminal internucleotide linkage is modified, however, up to all the internucleotide linkages in the oligonucleotide probe may be modified. Such internucleotide modifications may include modified linkages of the type used in the synthesis of anti-sense oligonucleotides. Examples of such nuclease resistant linkages include phosphorothioate linkages and methylphosphonate linkages, e.g., Oligonucleotides and Analogs, Chaps. 4-5, 6, respectively, IRL Press, New York (1991); boranophosphate linkages, e.g., Shaw et al., Methods Mol. Biol. 20: 225 43 (1993); polyamide nucleic acid (PNA) linkages, e.g., Nielsen et al., Science, 254: 1497 1500 (1991), and other like exonuclease resistant linkages. In embodiments where the polymerase mixture possesses a 3'→5' exonuclease functionality, it may be desirable to conduct hydrolysis probe assays in the presence of probes having a 3' protecting functionality.

The probes may target different alleles of a gene. The different alleles may, by way of non-limiting examples, be single nucleotide polymorphisms, or other types of alleles of a polymorphic gene. When multiple probes are used within a single mixture, there may be one pair of primers that span the regions of all probes or there may be a plurality of pairs of primers wherein some pairs span target regions that correspond to fewer than all of the probes.

In one embodiment, the mixture is used in an assay in which one or more hydrolysis probes such as those used in connection with Taqman® chemistry are present. The probes may contain a fluorophore that is covalently attached to one end of the oligonucleotide. A quencher may be attached at the other end of each probe. Examples of fluorophores include, but are not limited to, 6-carboxyfluorescein and tetrachlorofluorescin. Examples of quenchers include, but are not limited to, tetramethylrhodamine and dihydroxycyclopyrroloindole tripeptide.

Initially, when the probe is added to a system and hybridizes to a target, the quencher molecule reduces signal emitted by the fluorophore when the assay is excited by the cycler's light source, e.g., Fluorescence Resonance Energy Transfer. As long as the fluorophore and the quencher are in proximity, quenching inhibits fluorescence signals.

As noted above, the probes may be designed to anneal within a DNA region that exhibits complementarity to the probe and has been amplified by a specific set of primers. Probes may be, e.g., 15-50 nucleotides in length or 20-40 nucleotides in length. Probes may have other molecules attached, e.g., to increase Tm, thereby allowing use of shorter probes. These probes can be, e.g., 6-nucleotides in length. Some polymerases are capable of amplifying DNA with very short primers. With such a polymerase the probe may also be very short even without any further modification. In these embodiments, the probe can be 6-30 nucleotides in length. After the probes are added to the system they may hybridize to regions of the target to which they exhibit complementarity. The polymerase then extends the primer and synthesizes the nascent strand. The 5'→3' exonuclease activity of the polymerase that contains this ability, i.e., the first enzyme, degrades the probe that has annealed to the template. Degradation of the probe releases and breaks the close proximity of the fluorophore to the quencher. This relieves the quenching effect and allows fluorescence of the fluorophore. The fluorescence may be detected by a real-time PCR thermal cycler. The measure of the fluorophore released is indicative of the amount of DNA template that is present in the sample.

In addition to the first enzyme, a second enzyme is present, but that second enzyme lacks or substantially lacks the 5' to 3' exonuclease activity. When the second enzyme synthesizes a nascent strand and reaches the probe, it will not be able to excise the probe because it lacks an exonuclease functionality. Consequently, that enzyme will not cause separation of the quencher and the fluorophore. The second enzyme being unable to excise the probe will over time disassociate from the template. The probe will only be excised after a first enzyme finds that template. This time period will be defined by both the concentration of total enzyme and the relative amounts of the first and second enzymes. Significantly, this time is long enough to allow a sufficient amount of mismatched probes that had temporarily hybridized with the template due to only partial sequence complementarity to disassociate from their templates before they have been acted upon by the first enzyme. In embodiments where the second enzyme also lacks 3'→5' exonuclease activity, the likelihood of degradation of mismatched probes is further decreased. In embodiments where the first and/or second enzyme has 3'→5' exonuclease activity, the presence of 3' protecting groups on the probe(s) may further decrease the likelihood of degradation of mismatched probes.

The methods can be applied using multiple probes in the same system that is designed to determine the presence of different alleles. This may be accomplished by using different labels on the different probes and thus gathering different information depending on the signal detected, e.g., four different color fluorescent resoluble dyes may be used. Because information from several sites can be obtained from a single reaction, when multiple probes are used, fewer steps are required than would be required with systems that use separate wells for each allele. As a result is higher sample throughput.

In some embodiments, the method may be directed to detecting an allele. This method comprises obtaining a target sample, where the target sample comprises a polynucleotide sequence; combining the sample with one of the aforementioned mixtures, at least one probe where the probe comprises a quencher moiety and a reporting moiety, a primer complementary to a sequence on the target sample where the region to which the primer is complementary is downstream of the region to which the probe is complementary, under condition in which the primer can be extended; and detecting a signal of the reporting moiety, where detection of the signal is indicative of the presence of the alleles. In some embodiments there is a second primer, and the first primer and the second primer span the target region of interest. As one of ordinary skill in the art appreciates, one primer will be complementary to a sequence on the target and be upstream of the probe, and the other primer will be the same as a region of the target that is upstream of a region to which the probe is complementary.

The nucleotide sequences that are analyzed may be obtained from public databases, commercial suppliers, or through extraction from cells, tissues, organs, or organisms. For example, they may come from eukaryotic or prokaryotic cells. Eukaryotic cells include but are not limited to those obtained from fungi, yeast, plants, protozoans, and animals that include but are not limited to mammals (e.g., humans, monkeys, horses, dogs, pigs, rats, cats and mice), birds, reptiles and amphibians. Mammalian cells include but are not limited to blood cells such as erythrocytes and leukocytes, endothelial cells, epithelial cells, neuronal cells, muscle cells, and connective tissue cells.

Having described the invention with a degree of particularity, examples are now provided. These examples are not intended to and should not be construed to limit the scope of the claims in any way.

For Examples 1-3, various 5'→3' exonuclease activity ratios were studied by using a constant total polymerase amount, and varying the ratio of an enzyme possessing 5'→3' exonuclease activity and an enzyme lacking or substantially lacking that exonuclease activity. In Examples 1-3, the total amount of enzyme was 150 units per milliliter (U/ml), and measurement was through a radioactive assay. The enzyme with exonuclease activity was Tbr polymerase with chemical hot start modification, and the enzyme lacking or substantially lacking exonuclease activity was mutated Tbr polymerase lacking 5'→3' exonuclease domain with chemical hot start modification.

The PCR protocol with pre read for fluorescence at 60° C., initial denaturation for 10 minutes at 95° C., 40 cycles including denaturation for 15 s at 95° C. and 1 minute annealing/extension and fluorescence data collection at 60°, and post read for fluorescence at 60° C. was used for Examples 1, 2 and 3.

The PCR protocol with pre read for fluorescence at 60° C., initial denaturation for 7 minutes at 95° C., 40 cycles including denaturation for 5 s at 95° C. and 30 seconds annealing/extension and fluorescence data collection at 60° and post read for fluorescence at 60° C. was used for Example 4.

Example 5 uses another enzyme composition. The PCR protocol with pre read for fluorescence at 25° C., initial denaturation for 7 minutes at 95° C., 40 cycles including denaturation for 5 s at 95° C. and 30 seconds annealing/extension and fluorescence data collection at 60° and post read for fluorescence at 25° C. was used for Example 5.

Example 1

Reduction of Amount of Enzyme with Exonuclease Activity

TXB18

Figure 2:
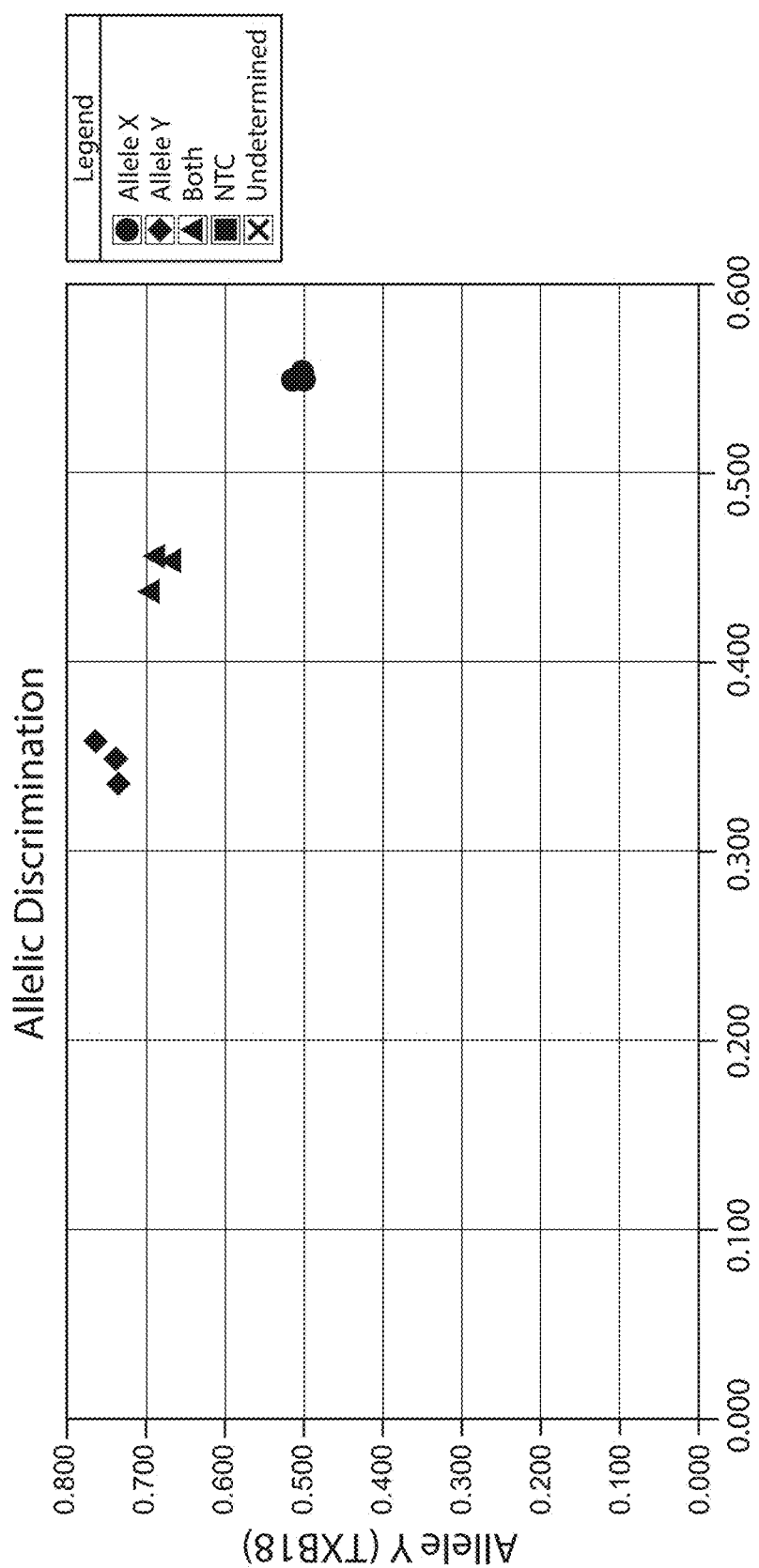
FIG. 2 shows experimental results in which the presence of all three genotypes for TXB18 was measured, and 33% of the polymerase used had exonuclease activity.

A set of DNA samples extracted from blood of volunteer donors representing three genotypes heterozygous, homozygous wild-type and homozygous mutant for TXB18 (C/T) SNP (rs 215938) were analyzed in triplicate. Wild type allele was detected with FAM™ dye labeled probe with the following sequence TGGGAACTTGCAGACGGAACA-CACAAAC (SEQ ID NO: 1) and mutant allele was detected with a Yakima Yellow™ labeled probe with following sequence TGGGAACTTGCAGATGGAACACACAAAC (SEQ ID NO: 2). Surprisingly, the enzyme mixture with least exonuclease activity gave the best discrimination. FIG. 1 shows the allelic discrimination when all of the polymerases possessed exonuclease activity. FIG. 2 shows the allelic discrimination when 33% of the polymerases possess exonuclease activity. Fluorescence intensity change between pre-read and post-read are plotted. Fluorescence from the FAM™ labeled probe is plotted on the y-axis and fluorescence from the Yakima Yellow™ labeled probe is plotted on the x-axis. Three clusters represent three different genotypes. Samples in a cluster showing high signal only from FAM™ dye labeled probe as high values in y-axis are homozygous wild types (diamonds), samples in a cluster showing high signal only from Yakima Yellow™ dye labeled probe as high signal on x-axis are homozygous mutants (circles) and samples in a cluster showing signal from both FAM™ and Yakima Yellow™ dye labeled probes are heterozygous (triangles). Comparison of results shown in FIGS. 1 and 2 show improved discrimination when 5'→3' exonuclease activity is adjusted to a lower level.

Example 2

Reduction of Amount of Enzyme with Exonuclease Activity

EIF2AK3

Figure 3:
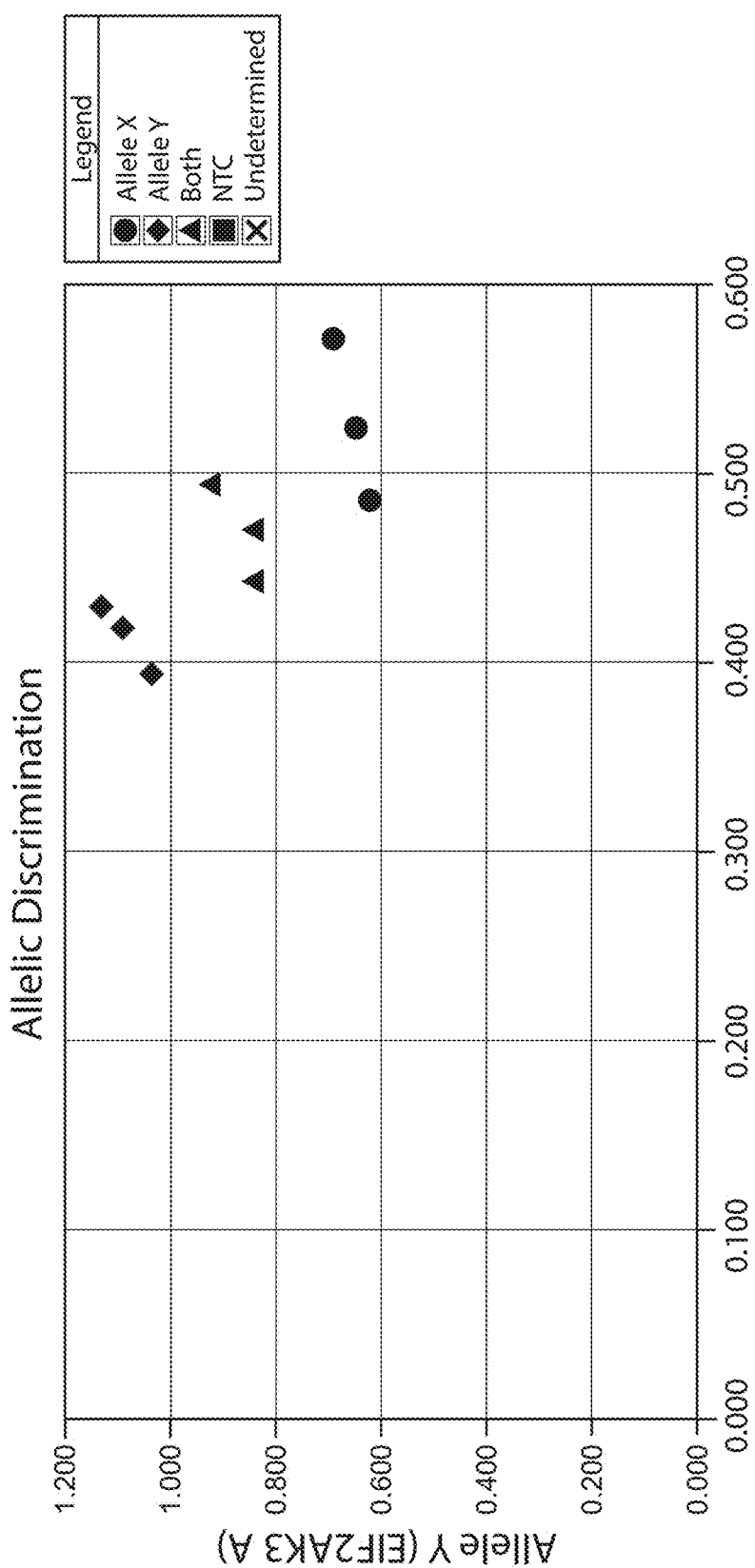
FIG. 3 shows experimental results in which the presence of all three genotypes for EIF2AK3 was measured, and 33% of the polymerase used had exonuclease activity.
Figure 4:
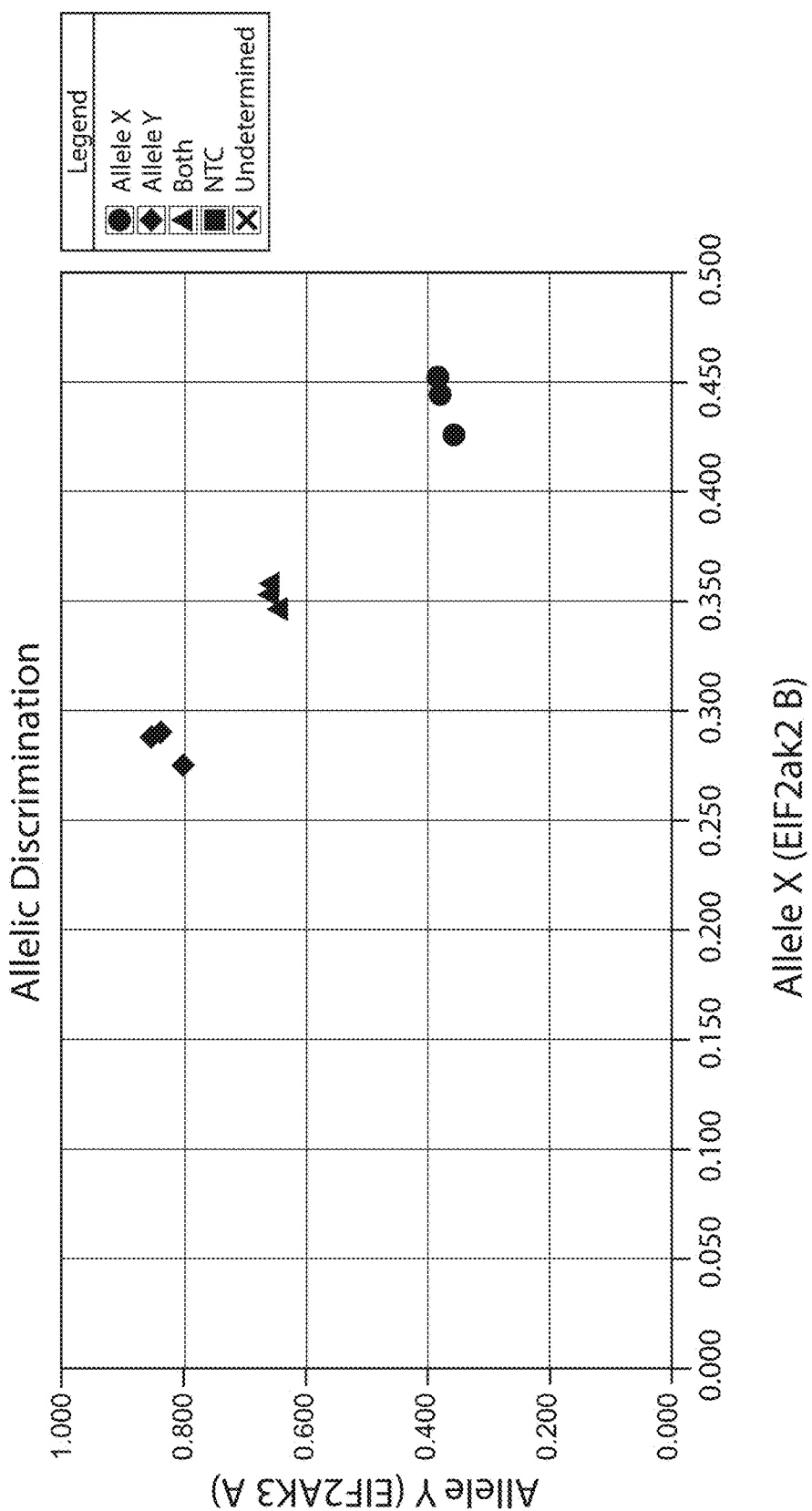
FIG. 4 shows experimental results in which the presence of all three genotypes for EIF2AK3 was measured, and 7% of the polymerase used had exonuclease activity.

A set of DNA samples extracted from blood of volunteer donors representing three genotypes, heterozygous, homozygous wild-type, and homozygous mutant, for EIF2AK3 (A/G rs7571971) were analyzed in triplicate. Wild type allele was detected with FAM™ dye labeled probe with following sequence TTGATGGACTGCACTGCTTCAT-GTGCTAC (SEQ ID NO: 3) and mutant allele was detected with a Yakima Yellow™ labeled probe with following sequence TTGATGGACTGCGCTGCTTCATGTGCTAC (SEQ ID NO: 4). FIG. 3 shows the allelic discrimination when 33% of the polymerases possessed exonuclease activity. By contrast, FIG. 4 shows the allelic discrimination when 7% of the polymerases possessed exonuclease activity. As the amount of polymerase with exonuclease activity dropped, the discrimination improved, demonstrated by the tighter clustering of points when less polymerase with exonuclease functionality is present.

Example 3

Reduction of Amount of Enzyme with Exonuclease Activity

NOTCH2

Figure 5:
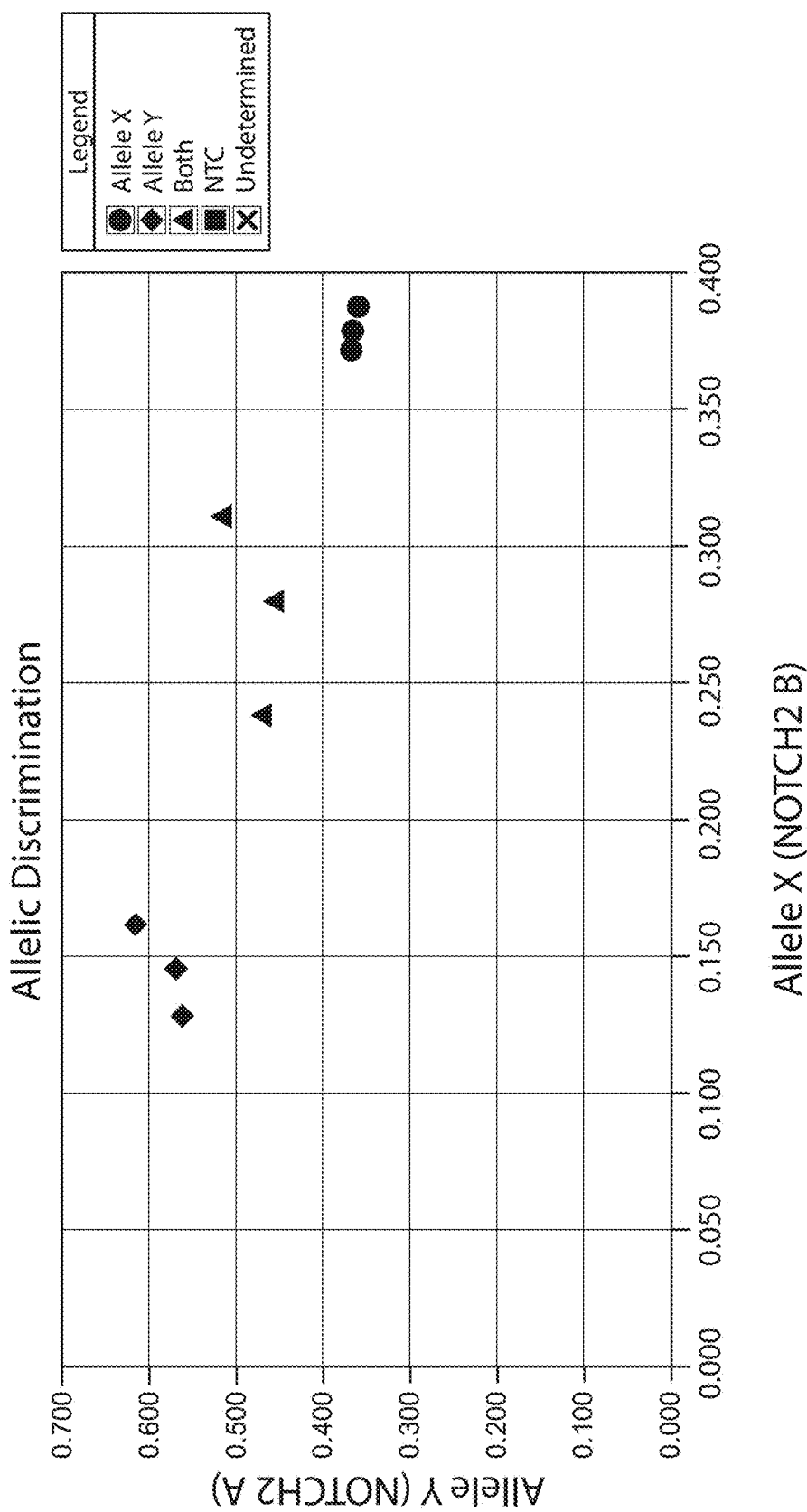
FIG. 5 shows experimental results in which the presence of all three genotypes for Notch2 was measured, and 33% of the polymerase used had exonuclease activity.
Figure 6:
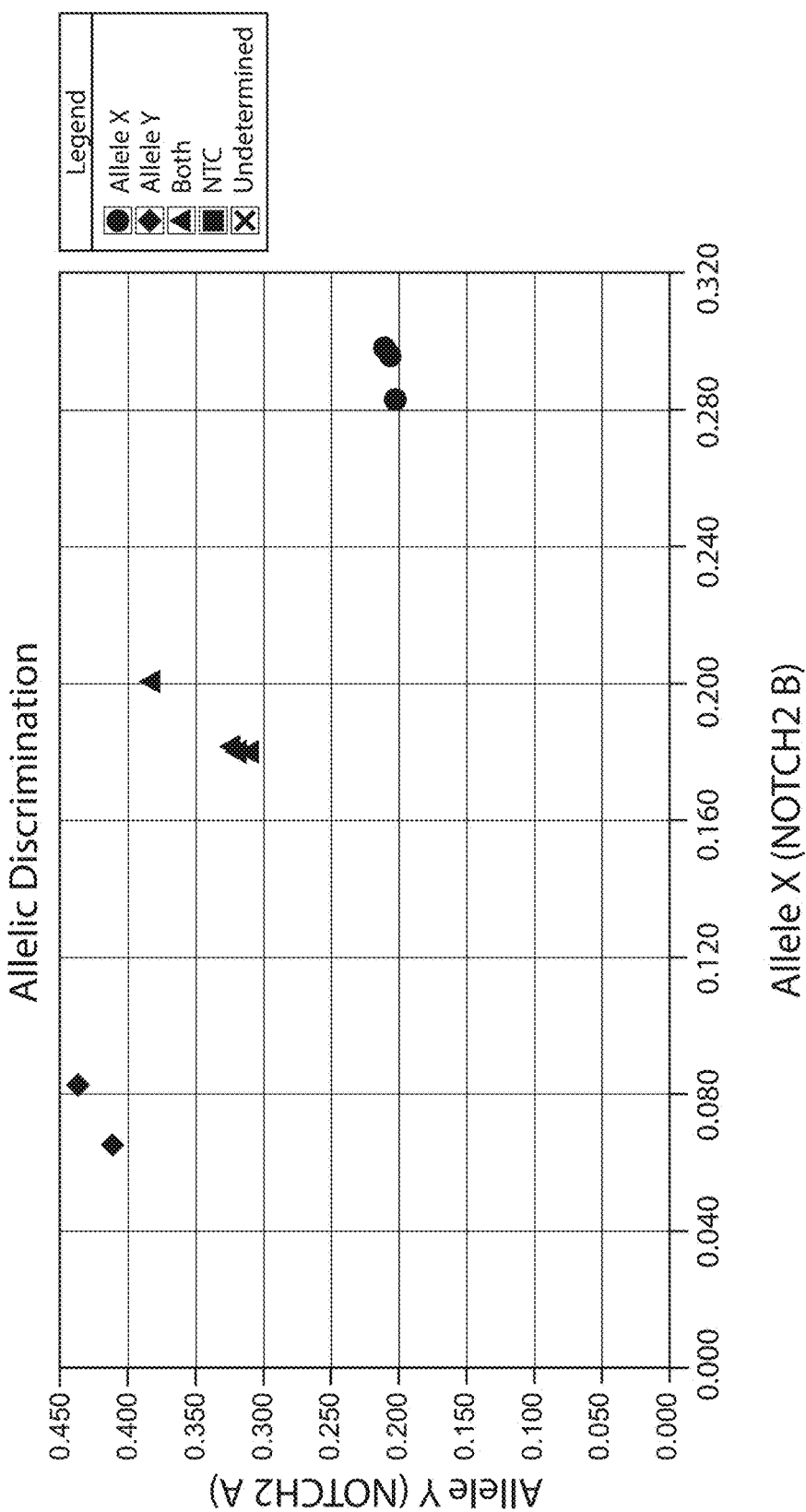
FIG. 6 shows experimental results in which the presence of all three genotypes for Notch2 was measured, and 7% of the polymerase used had exonuclease activity.

A set of DNA samples extracted from blood of volunteer donors representing three genotypes, heterozygous, homozygous wild-type, and homozygous mutant for NOTCH2 (A/G rs2453042) were analyzed in triplicate. Wild type allele was detected with FAM™ dye labeled probe with following sequence CAGGTTGAGTGATTTATGCAGA-CATTTGGT (SEQ ID NO: 5) and mutant allele was detected with a Yakima Yellow™ labeled probe with following sequence CAGGTTGAGTGATTTACGCAGA-CATTTGGT (SEQ ID NO: 6). FIG. 5 shows the allelic discrimination when 33% of the polymerase possessed exonuclease activity. By contrast, FIG. 6 shows the allelic discrimination when 7% of the polymerase possessed exonuclease activity. As with Example 2, decreasing the amount of polymerase with exonuclease activity increased the discrimination.

Example 4

Increase of Total Enzyme Amount

EIF2AK3

Figure 7:
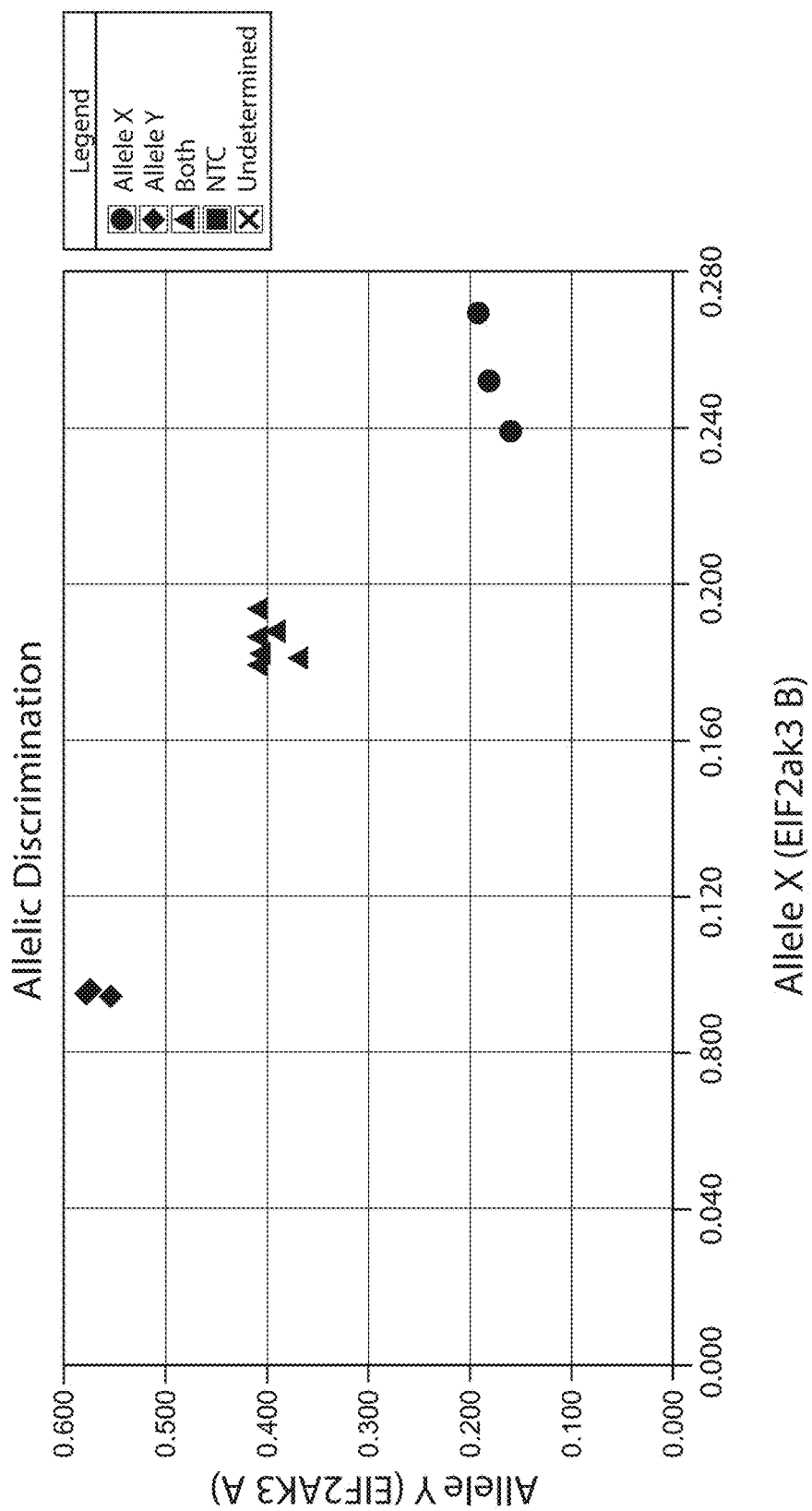
FIG. 7 shows experimental results in which the presence of all three genotypes for EIF2AK3 was measured, and 3.3% of the polymerase used had exonuclease activity.

The same set of samples as in Example 2, representing the three genotypes of EIF2AK3, was probed with different reaction conditions. The amount of polymerase having exonuclease was further reduced to 3.3%, the concentration of total enzyme was increased to 450 units per milliliter, and annealing-extension time was reduced from 1 minute to 30 seconds, as shown in FIG. 7. The results shown in FIGS. 4 and 7 demonstrated that the increase in total amount of enzyme, while exonuclease activity is kept low, further improved discrimination and improved discrimination was achieved in reduced time.

Example 5

Enhanced Discrimination Using Tbr and Modified PHUSION® Polymerase Mix

Figure 8:
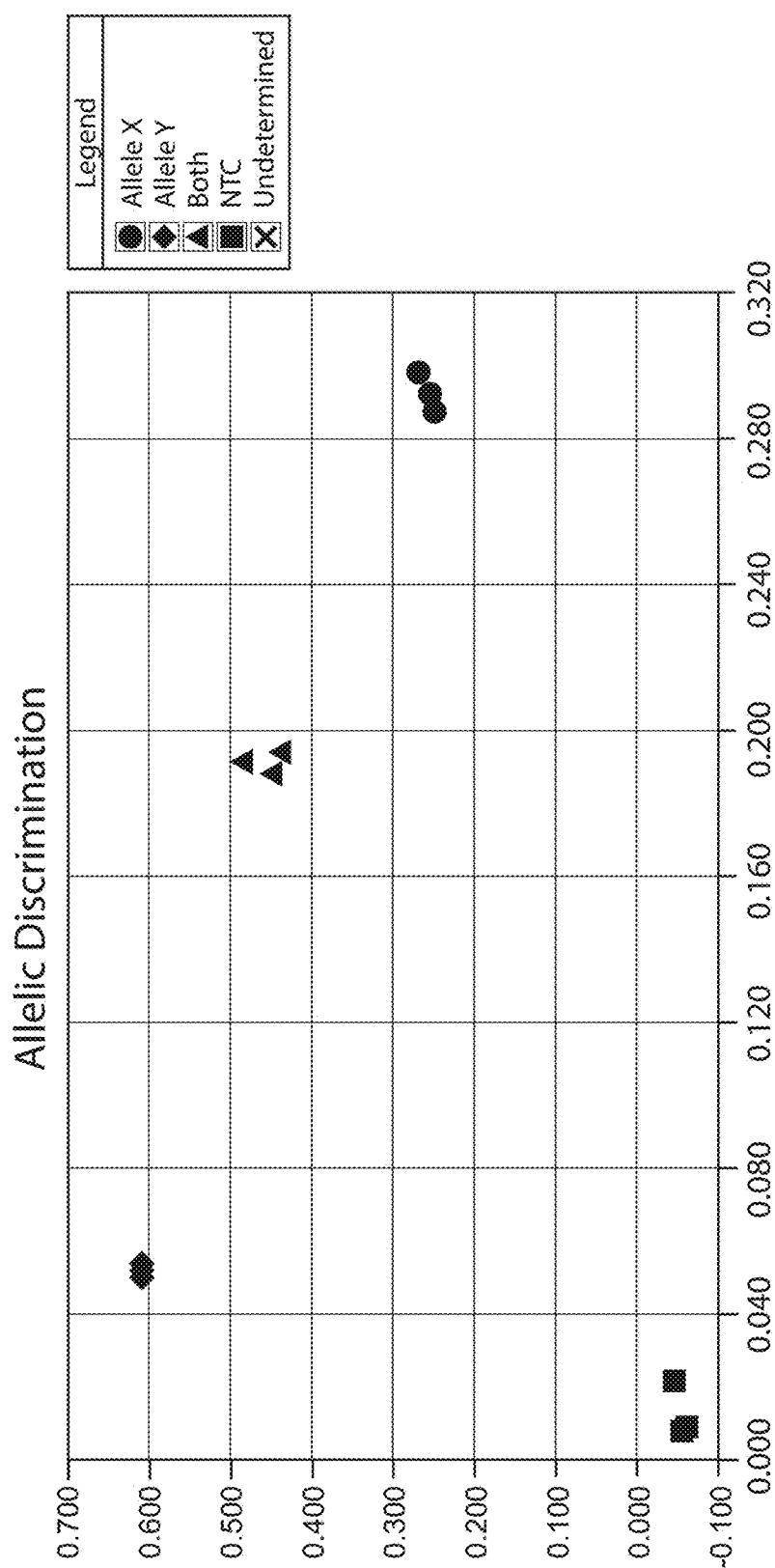
FIG. 8 shows experimental results in which the presence of all three genotypes for Notch2 was measured, and the polymerase mixture comprised Tbr polymerases.
Figure 9:
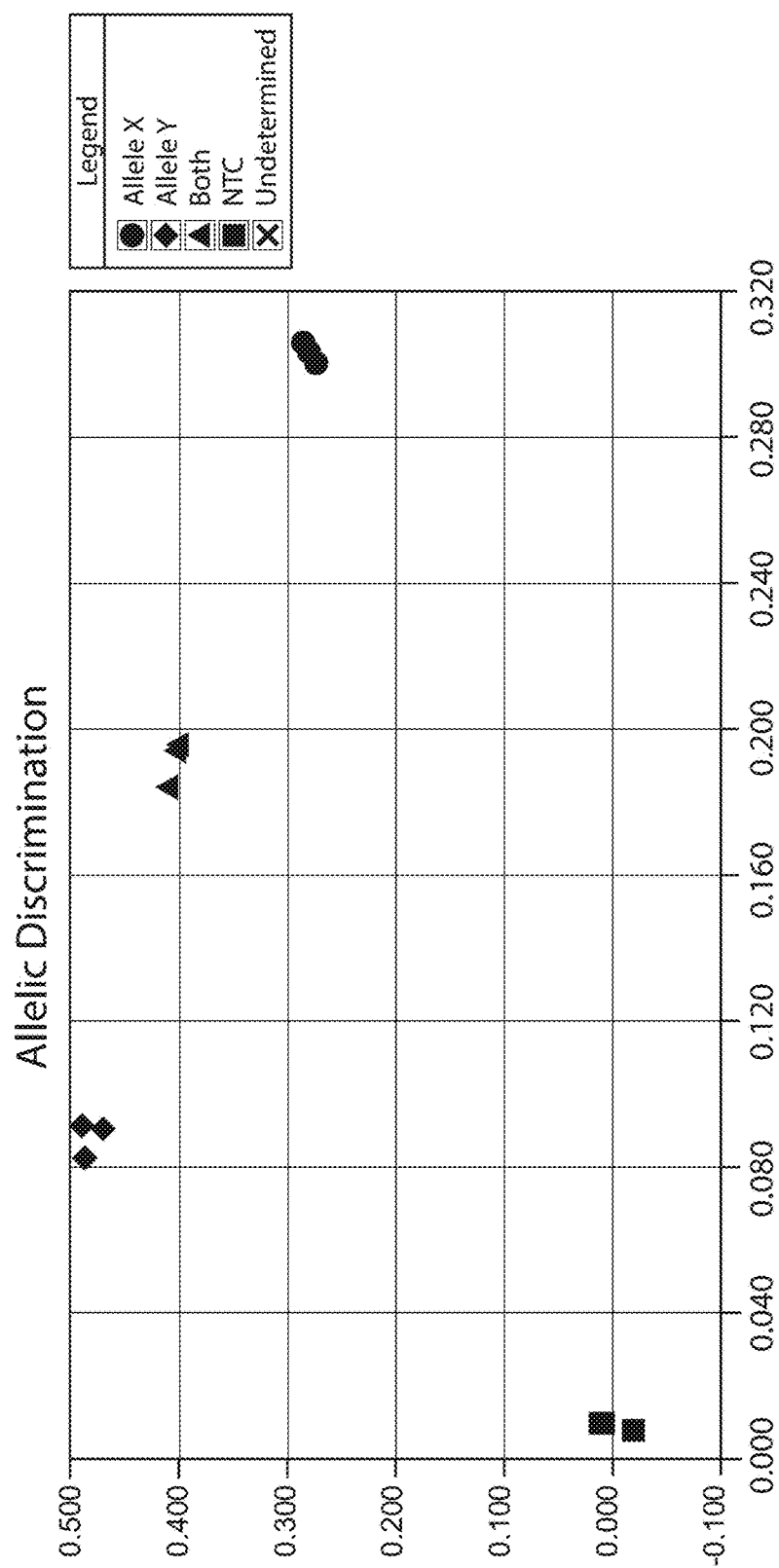
FIG. 9 shows experimental results in which the presence of all three genotypes for Notch2 was measured, and the polymerase mixture comprised Tbr and fusion polymerases.

A set of DNA samples extracted from blood of volunteer donors representing three genotypes, heterozygous, homozygous wild-type, and homozygous mutant for NOTCH2 (A/G rs2453042) were analyzed in triplicate. Wild type allele was detected with FAM™ dye labeled probe with following sequence CAGGTTGAGTGATTTATGCAGACATTTGGT (SEQ ID NO: 5) and mutant allele was detected with a Yakima Yellow™ labeled probe with following sequence CAGGTTGAGTGATTTACGCAGACATTTGGT (SEQ ID NO: 6). FIG. 8 shows the allelic discrimination with polymerase mix where both polymerases are Tbr based. FIG. 9 shows the allelic discrimination with polymerase mix where first polymerase is Tbr based and the second is modified PHUSION® DNA polymerase lacking both 3'→5' exonuclease and 5'→3' exonuclease activities. In both cases, polymerase mixes contain 3% of the Tbr polymerase possessing exonuclease activity.

Example 6

Figure 10:
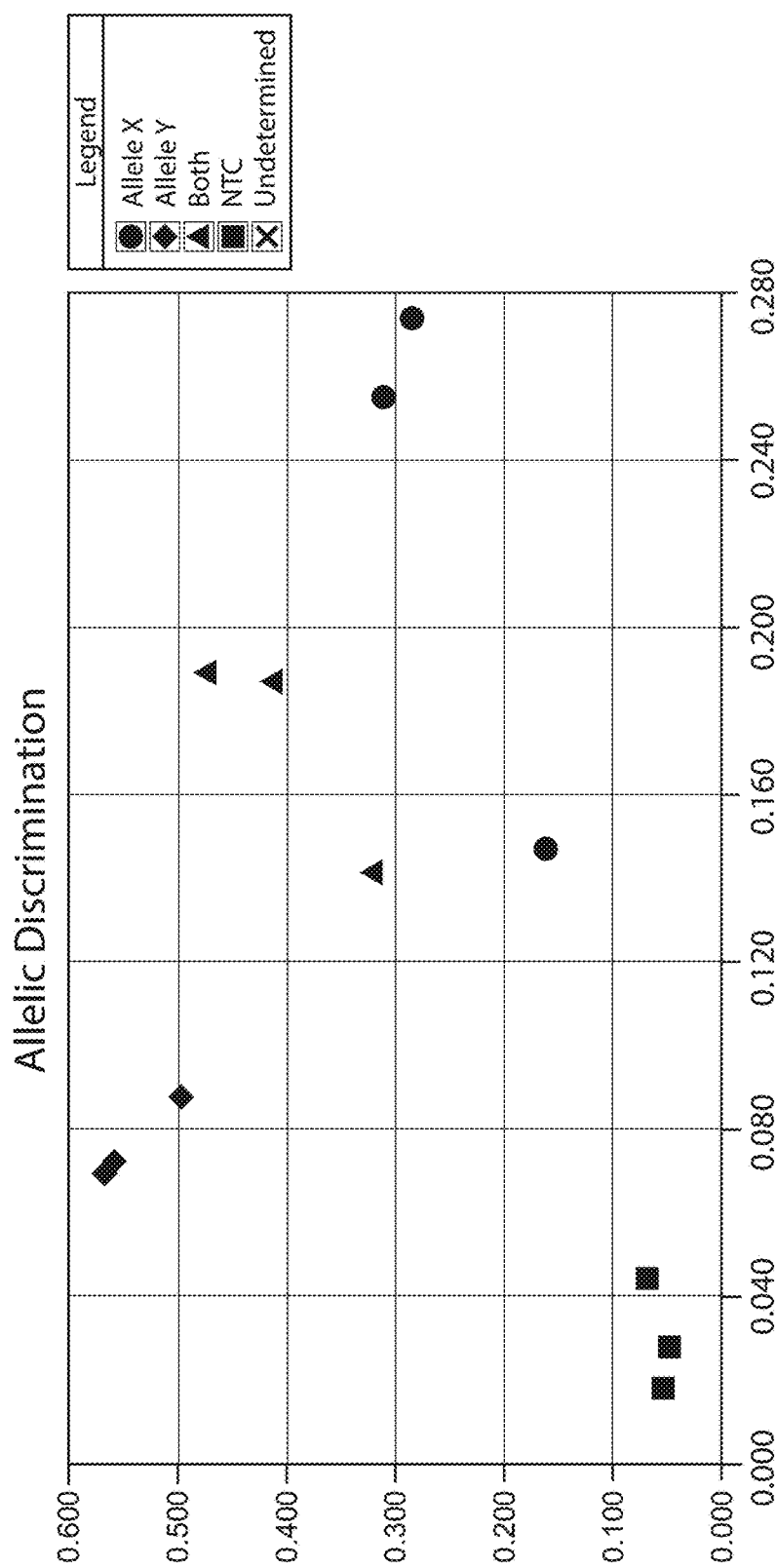
FIG. 10 shows experimental results in which the presence of all three genotypes for Notch2 was measured in the presence of an inhibitor.
Figure 11:
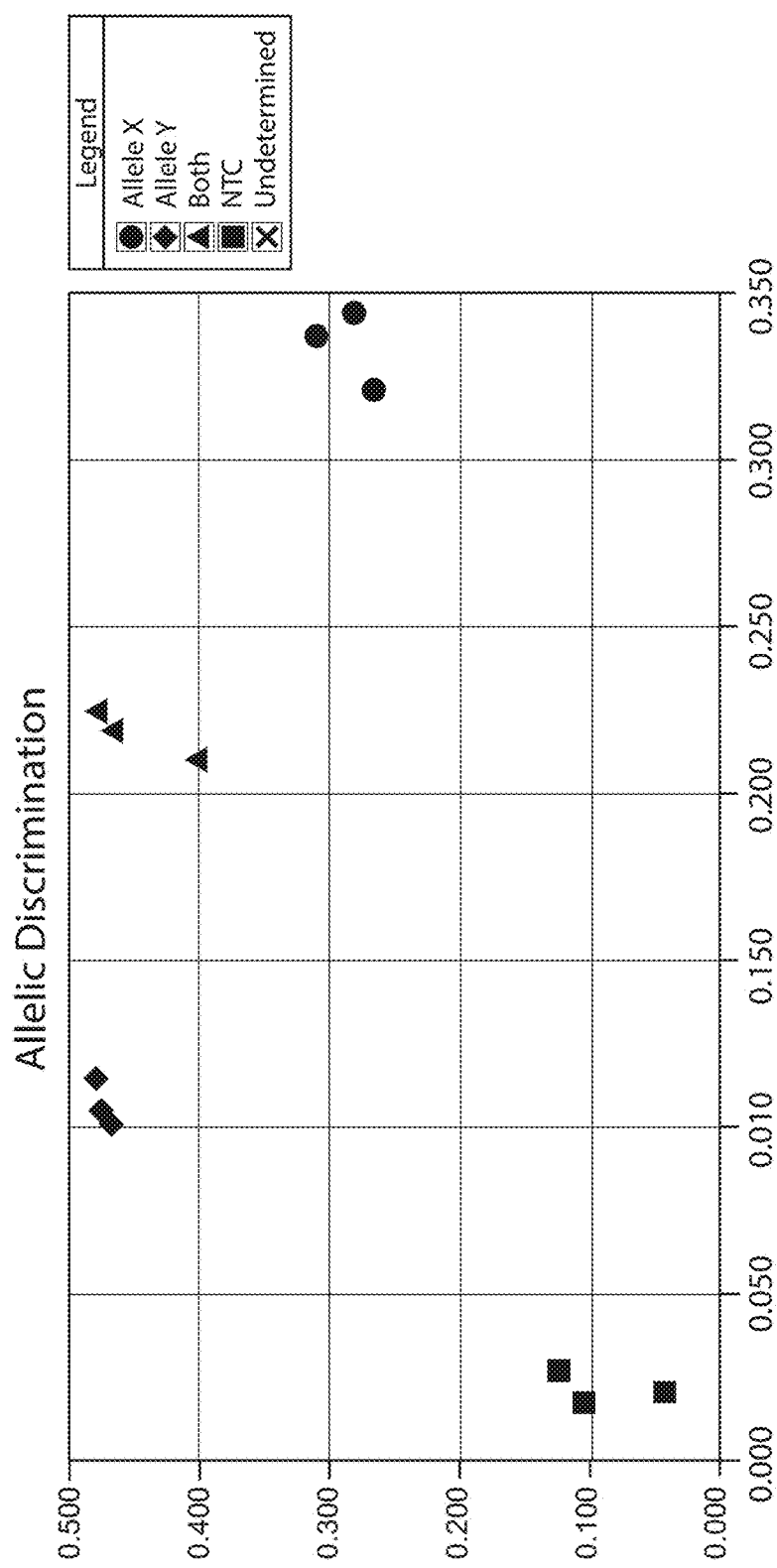
FIG. 11 shows experimental results in which the presence of all three genotypes for Notch2 was measured in the presence of an inhibitor.

Enhanced Discrimination Using Tbr and PHUSION® Polymerase Mixture in the Presence of Inhibitor A set of DNA samples extracted from blood of volunteer donors representing three genotypes, heterozygous, homozygous wild-type, and homozygous mutant for NOTCH2 (A/G rs2453042) were analyzed in triplicate. Wild type allele was detected with FAM™ dye labeled probe with following sequence CAGGTTGAGTGATTTATGCAGACATTTGGT (SEQ ID NO: 5) and mutant allele was detected with a Yakima Yellow™ labeled probe with following sequence CAGGTTGAGTGATTTACGCAGACATTTGGT (SEQ ID NO: 6). FIG. 10 shows the allelic discrimination in the presence of spiked inhibitor sample with polymerase mix where both polymerases are Tbr based. FIG. 11 shows the allelic discrimination in the presence of spiked inhibitor sample with polymerase mix where first polymerase is Tbr based and the second is PHUSION® DNA polymerase lacking both 3'→5' exonuclease and 5'→3' exonuclease activities. In both cases, the polymerase mixes contain 3% of the Tbr polymerase possessing exonuclease activity. The spiked inhibitor was a 0.5 mm punch of Ficus Benjamina leaf.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

Applicants incorporate by reference the material contained in the accompanying computer readable Sequence Listing identified as EnzymeMixture_ST25.txt, having a file creation date of Sep. 23, 2011 at 12:13:29 P.M. and file size of 1.31 kilobytes.

What is claimed is:

1. A composition comprising
   a first DNA polymerase, wherein the first polymerase has a 5'→3' exonuclease activity; and
   a second DNA polymerase, wherein the second polymerase lacks or substantially lacks a 5'→3' exonuclease activity, and
   at least one hydrolysis probe comprising a quencher moiety and a reporter moiety, and optionally a 3' modification,
   the combined amount of first and second polymerases in the composition is between 100 polymerase activity units per milliliter and 500 polymerase activity units per milliliter, the ratio of the first polymerase to the second polymerase in the composition is 1:99 to 1:19.

2. The composition of claim 1 wherein the first polymerase is Tbr polymerase and the second polymerase is Tbr polymerase comprising a modification that deactivates or substantially deactivates 5'→3' exonuclease activity.

3. The composition of claim 1 wherein the at least one reporter moiety is a fluorescent dye and the fluorescent dye on each of the hydrolysis probes exhibits distinguishable spectral properties, wherein the quencher is capable of quenching fluorescence of the fluorescent dye, and wherein the 3' modification of the hydrolysis probes renders the hydrolysis probes less susceptible to 3'→5' exonuclease degradation.

4. The composition of claim 1 wherein the hydrolysis probes anneals to different alleles of a gene, wherein the different alleles are alleles of a polymorphic gene.

5. The composition of claim 4 wherein the different alleles are single nucleotide polymorphisms.

6. The composition of claim 1 wherein the first polymerase, the second polymerase, or both the first and the second polymerase lacks or substantially lacks 3'→5' exonuclease activity, or has less 3→5' exonuclease activity than a wild type.

7. A method for detecting an allele of a target nucleic acid comprising
combining a target nucleic acid with a mixture of a first polymerase having a 5'→3' exonuclease activity and a second polymerase lacking or substantially lacking a 5'→3' exonuclease activity, where the ratio of the first polymerase to the second polymerase in the mixture is 1:99 to 1:19, and the combined amount of first polymerase and second polymerase is between 100 polymerase activity units per milliliter and 500 polymerase activity units per milliliter,
at least a first hydrolysis probe wherein the first probe is capable of annealing to a portion of the target nucleic acid containing a first form of an allele present in the target nucleic acid, and comprising a quencher moiety and a first reporter moiety,
a primer, wherein the primer is complementary to a sequence on the target nucleic acid upstream of the portion of the target nucleic acid complementary to the first probe, under conditions in which the primer can be extended, such that extension of the primer results in degradation of an annealed first probe and separation of the quencher moiety from the first reporter moiety, and resulting in a first signal from the first reporter moiety of the first probe; and
detecting the first signal from the first reporter moiety of the first probe, wherein detection of the first signal is indicative of the presence of the first form of the allele.

8. The method of claim 7 further comprising a second probe, wherein the second probe is capable of annealing to a portion of the target nucleic acid containing a second form of the allele present in the target nucleic acid, and comprising a quencher moiety and a second reporter moiety, and wherein degradation of an annealed second probe by extension of the upstream-annealing primer separates the quencher moiety from the second reporter moiety, resulting in a second signal from the second reporter moiety of the second probe; and detecting the second signal from the second reporter moiety of the second probe, which is distinguishable from the first signal, wherein detection of the second signal is indicative of the presence of the second form of the allele.

9. The method of claim 8 wherein a comparison of the first signal and the second signal allows for allelic discrimination of the target nucleic acid.

10. The method of claim 7 wherein the first polymerase is Tbr, and possesses a 5'→3' exonuclease activity, and the second polymerase is Tbr, and lacks or substantially lacks a 5'→3' exonuclease activity.

11. The method of claim 7 wherein the first polymerase, the second polymerase, or both the first and the second polymerase lacks or substantially lacks a 3'→5' exonuclease activity, or has less 3'→5' exonuclease activity than the wild type counterpart of the first polymerase, the second polymerase, or the first and second polymerases, respectively.

12. The method of claim 7 wherein at least one of the first polymerase or the second polymerase is a fusion polymerase.

13. The method of claim 12 wherein the fusion polymerase comprises a sequence-nonspecific double-stranded nucleic acid binding protein.

14. The method of claim 12 wherein the fusion polymerase comprises a sequence-nonspecific nucleic acid binding domain derived from Sac7d or Sso7d.

15. The method of claim 7 further comprising combining a reagent capable of creating a hot start condition with the polymerase mixture.

16. A kit comprising
a polymerase mixture, the mixture comprising at least a first DNA polymerase that possesses a 5'→3' exonuclease activity and at least a second DNA polymerase that lacks or substantially lacks a 5'→3' exonuclease activity, where the ratio of the first polymerase to the second polymerase in the mixture is 1:99 to 1:19, and the combined amount of first polymerase and second polymerase is between 100 polymerase activity units per milliliter and 500 polymerase activity units per milliliter, and
at least one hydrolysis probe comprising a quencher moiety and a reporter moiety, and optionally a 3' modification.

17. The kit of claim 16 wherein the first polymerase is Tbr polymerase and the second polymerase is Tbr polymerase comprising a modification that deactivates or substantially deactivates 5'→3' exonuclease activity.

18. A method for increasing the fidelity of allelic determination of a target nucleic acid using a dual-labeled probe, the method comprising
contacting the target nucleic acid with a mixture of a first polymerase having a 5'→3' exonuclease activity and a second polymerase lacking or substantially lacking a 5'→3' exonuclease activity, at least one hydrolysis probe, and at least one primer, where the ratio of the first polymerase to the second polymerase in the mixture is 1:99 to 1:19, and the combined amount of first polymerase and second polymerase is between 100 polymerase activity units per milliliter and 500 polymerase activity units per milliliter,
where the at least one probe is capable of annealing to a portion of the target nucleic acid containing the allele, and the probe comprises a quencher moiety and a reporter moiety,
where the primer is complementary to a sequence of the target nucleic acid which is upstream of the sequence to which the probe is complementary, under conditions in which the primer can be extended such that extension of the primer degrades an annealed probe and separates the quencher moiety from the reporter moiety; and
detecting a signal from the reporter moiety indicating the presence of the allele, where the method decreases the number of false positive results generated by a misannealed probe by balancing the levels of 5'→3' exonuclease and polymerase activities in the mixture.

19. The method of claim 18 wherein the first polymerase is Tbr and possesses a 5'→3' exonuclease activity, and the second polymerase is Tbr and lacks or substantially lacks a 5'→3' exonuclease activity.

20. The method of claim 18 wherein at least one of the first polymerase or the second polymerase is a fusion polymerase.

21. A hydrolysis probe assay method comprising
combining a target nucleic acid with a polymerase mixture comprising at least two polymerase enzymes, at least one hydrolysis probe comprising a quencher moiety and a reporter moiety and optionally a 3' modification, and at least one primer, where the ratio of the first polymerase to the second polymerase in the mixture is 1:99 to 1:19, and the combined amount of first polymerase and second polymerase is between 100 polymerase activity units per milliliter and 500 polymerase activity units per milliliter,
amplifying the target nucleic acid using a polymerase chain reaction and the at least one primer, and
degrading the at least one labeled probe annealed to the target nucleic acid, wherein the amplification step is dependent on a polymerase activity of the polymerase mixture and the degradation step is dependent on a 5'→3' exonuclease activity of the polymerase mixture, and wherein at least one of the polymerase enzymes of the polymerase mixture possesses a 5'→3' exonuclease activity and at least one of the polymerase enzymes of the polymerase mixture lacks or substantially lacks a 5'→3' exonuclease activity, such that the amount of a product formed in the amplification step is dependent on the total amount of polymerase activity in the mixture, and the amount of probe hydrolyzed in the degradation step is dependent on the ratio of polymerase enzyme(s) possessing 5'→3' exonuclease activity and polymerase enzyme lacking or substantially lacking 5'→3' exonuclease activity in the polymerase mixture.

22. The kit of claim 16 where the ratio of the first polymerase to the second polymerase in the mixture is 1:32 to 1:24.

23. The composition of claim 1 where the ratio of the first polymerase to the second polymerase in the composition is 1:32 to 1:24.

24. A composition comprising
a first DNA polymerase, wherein the first polymerase has a 5'→3' exonuclease activity;
a second DNA polymerase, wherein the second polymerase lacks or substantially lacks a 5'→3' exonuclease activity, and
at least one hydrolysis probe wherein each hydrolysis probe comprises at least one of at least one label, a quencher, or a 3' modification, wherein the at least one label is a fluorescent dye and the fluorescent dye on each of the hydrolysis probes exhibits distinguishable spectral properties, wherein the quencher is capable of quenching fluorescence of the fluorescent dye, and wherein the 3' modification of the hydrolysis probe renders the hydrolysis probes less susceptible to 3'→5' exonuclease degradation, wherein
the combined amount of first and second polymerases in the composition is between 100 polymerase activity units per milliliter and 500 polymerase activity units per milliliter, the ratio of the first polymerase to the second polymerase in the composition is 1:99 to 1:19, wherein the first polymerase is Tbr polymerase and the second polymerase is Tbr polymerase comprising a modification that deactivates or substantially deactivates 5'→3' exonuclease activity, and wherein the first polymerase, the second polymerase, or both the first and the second polymerase lacks or substantially lacks 3'→5' exonuclease activity, or has less 3'→5' exonuclease activity than a wild type Tbr polymerase.

25. The composition of claim 2 wherein the modification that deactivates or substantially deactivates 5'→3' exonuclease activity is at least one mutation in the second polymerase.

26. The kit of claim 17 wherein the modification that deactivates or substantially deactivates 5'→3' exonuclease activity is at least one mutation in the second polymerase.

27. The composition of claim 25 wherein the at least one mutation in the second polymerase comprises a mutation in a conserved A(V/T)YG domain (SEQ ID NO: 7).

28. The kit of claim 26 wherein the at least one mutation in the second polymerase comprises a mutation in a conserved A(V/T)YG domain (SEQ ID NO: 7).

29. The composition of claim 2 wherein the modification that deactivates or substantially deactivates 5'→3' exonuclease activity is a blocking moiety in association with the second polymerase.

30. The composition of claim 29 wherein the blocking moiety irreversibly binds to a 5'→3' exonuclease site of Tbr or binds elsewhere on Tbr but causes a change in configuration that renders the 5'→3' exonuclease site inactive.

31. The kit of claim 17 wherein the modification that deactivates or substantially deactivates 5'→3' exonuclease activity is a blocking moiety in association with the second polymerase.

32. The kit of claim 31 wherein the blocking moiety irreversibly binds to a 5'→3' exonuclease site of Tbr or binds elsewhere on Tbr but causes a change in configuration that renders the 5'→3' exonuclease site inactive.

33. A composition comprising
a first DNA polymerase, wherein the first polymerase has a 5'→3' exonuclease activity; and
a second DNA polymerase, wherein the second polymerase lacks or substantially lacks a 5'→3' exonuclease activity, wherein the second polymerase is a fusion polymerase, and
the combined amount of first and second polymerases in the composition is between 100 polymerase activity units per milliliter and 500 polymerase activity units per milliliter, the ratio of the first polymerase to the second polymerase in the composition is 1:99 to 1:19, wherein a blocking moiety in association with the second polymerase deactivates or substantially deactivates 5'→3' exonuclease activity of the second polymerase.

34. The composition of claim 33 wherein the blocking moiety irreversibly binds to a 5'→3' exonuclease site of the second polymerase or binds elsewhere on the second polymerase but causes a change in configuration that renders the 5'→3' exonuclease site inactive.

35. The composition of claim 33 further comprising at least one hydrolysis probe wherein each hydrolysis probe comprises at least one of at least one label, a quencher, or a 3' modification, wherein the at least one label is a fluorescent dye and the fluorescent dye on each of the hydrolysis probes exhibits distinguishable spectral properties, wherein the quencher is capable of quenching fluorescence of the fluorescent dye, and wherein the 3' modification of the hydrolysis probes renders the hydrolysis probes less susceptible to 3'→5' exonuclease degradation.

36. The composition of claim 35 wherein the at least one hydrolysis probe anneals to different alleles of a gene, wherein the different alleles are alleles of a polymorphic gene.

37. The composition of claim 36 wherein the different alleles are single nucleotide polymorphisms.

38. The composition of claim 33 wherein the first polymerase, the second polymerase, or both the first and the second polymerase lacks or substantially lacks 3'→5' exonuclease activity, or has less 3'→5' exonuclease activity than a wild type.

39. The composition of claim 33 wherein the ratio of the first polymerase to the second polymerase in the composition is 1:32 to 1:24.

40. The composition of claim 24 wherein the modification that deactivates or substantially deactivates 5'→3' exonuclease activity is at least one mutation in the second polymerase.

41. The composition of claim 40 wherein the at least one mutation in the second polymerase comprises a mutation in a conserved A(V/T)YG domain (SEQ ID NO: 7).

42. A composition comprising
a first DNA polymerase, wherein the first polymerase has a 5'→3' exonuclease activity; and
a second DNA polymerase, wherein the second polymerase lacks or substantially lacks a 5'→3' exonuclease activity,
wherein the combined amount of first and second polymerases in the composition is between 100 polymerase activity units per milliliter and 500 polymerase activity units per milliliter, the ratio of the first polymerase to the second polymerase in the composition is 1:99 to 1:19, wherein the first polymerase is Tbr polymerase and the second polymerase is Tbr polymerase comprising a modification that deactivates or substantially deactivates 5'→3' exonuclease activity, and wherein the first polymerase, the second polymerase, or both the first and the second polymerase lacks or substantially lacks 3'→5' exonuclease activity, or has less 3'→5' exonuclease activity than a wild type Tbr polymerase, and
wherein the modification that deactivates or substantially deactivates 5'→3' exonuclease activity is a blocking moiety in association with the second polymerase.

43. The composition of claim 42 wherein the blocking moiety irreversibly binds to a 5'→3' exonuclease site of the second polymerase or binds elsewhere on the second polymerase but causes a change in configuration that renders the 5'→3' exonuclease site inactive.

44. The composition of claim 24 wherein the at least one hydrolysis probe anneals to different alleles of a gene, wherein the different alleles are alleles of a polymorphic gene.

45. The composition of claim 44 wherein the different alleles are single nucleotide polymorphisms.

46. The composition of claim 24 wherein the ratio of the first polymerase to the second polymerase in the composition is 1:32 to 1:24.

47. A kit comprising
a polymerase mixture, the mixture comprising at least a first Tbr DNA polymerase that possesses a 5'→3' exonuclease activity and at least a second Tbr DNA polymerase that lacks or substantially lacks a 5'→3' exonuclease activity, wherein the first polymerase, the second polymerase, or both the first and the second polymerase lacks or substantially lacks 3'→5' exonuclease activity, or has less 3'→5' exonuclease activity than a wild type Tbr DNA polymerase, and where the ratio of the first polymerase to the second polymerase in the mixture is 1:99 to 1:19, and the combined amount of first polymerase and second polymerase is between 100 polymerase activity units per milliliter and 500 polymerase activity units per milliliter; and
at least one hydrolysis probe wherein each hydrolysis probe comprises at least one of at least one label, a quencher, or a 3' modification, wherein the at least one label is a fluorescent dye and the fluorescent dye on each of the hydrolysis probes exhibits distinguishable spectral properties, wherein the quencher is capable of quenching fluorescence of the fluorescent dye, and wherein the 3' modification of the hydrolysis probes renders the hydrolysis probes less susceptible to 3'→5' exonuclease degradation and the instructions further comprise annealing the probe to a portion of the target nucleic acid.

48. The kit of claim 47 wherein the modification that deactivates or substantially deactivates 5'→3' exonuclease activity is at least one mutation in the second polymerase.

49. The kit of claim 48 wherein the at least one mutation in the second polymerase comprises a mutation in a conserved A(V/T)YG domain (SEQ ID NO: 7).

50. A kit comprising
a polymerase mixture, the mixture comprising at least a first Tbr DNA polymerase that possesses a 5'→3' exonuclease activity and at least a second Tbr DNA polymerase that lacks or substantially lacks a 5'→3' exonuclease activity, wherein the first polymerase, the second polymerase, or both the first and the second polymerase lacks or substantially lacks 3'→5' exonuclease activity, or has less 3'→5' exonuclease activity than a wild type Tbr DNA polymerase, and where the ratio of the first polymerase to the second polymerase in the mixture is 1:99 to 1:19, and the combined amount of first polymerase and second polymerase is between 100 polymerase activity units per milliliter and 500 polymerase activity units per milliliter,
wherein the modification that deactivates or substantially deactivates 5'→3' exonuclease activity is a blocking moiety in association with the second polymerase.

51. The kit of claim 50 wherein the blocking moiety irreversibly binds to a 5'→3' exonuclease site of Tbr or binds elsewhere on Tbr but causes a change in configuration that renders the 5'→3' exonuclease site inactive.

52. The kit of claim 47 where the ratio of the first polymerase to the second polymerase in the mixture is 1:32 to 1:24.

53. A kit comprising
a polymerase mixture, the mixture comprising at least a first DNA polymerase that possesses a 5'→3' exonuclease activity and at least a second DNA polymerase that lacks or substantially lacks a 5'→3' exonuclease activity, wherein the second polymerase is a fusion polymerase, wherein a blocking moiety in association with the second polymerase deactivates or substantially deactivates 5'→3' exonuclease activity of the second polymerase, and where the ratio of the first polymerase to the second polymerase in the mixture is 1:99 to 1:19, and the combined amount of first polymerase and second polymerase is between 100 polymerase activity units per milliliter and 500 polymerase activity units per milliliter.

54. The kit of claim 53 further comprising at least one hydrolysis probe wherein each hydrolysis probe comprises at least one of at least one label, a quencher, or a 3' modification, wherein the at least one label is a fluorescent dye and the fluorescent dye on each of the hydrolysis probes exhibits distinguishable spectral properties, wherein the quencher is capable of quenching fluorescence of the fluorescent dye, and wherein the 3' modification of the hydrolysis probes renders the hydrolysis probes less susceptible to 3'→5' exonuclease degradation and the instructions further comprise annealing the probe to a portion of the target nucleic acid.

55. The kit of claim 53 wherein the blocking moiety irreversibly binds to a 5'→3' exonuclease site of the second polymerase or binds elsewhere on the second polymerase but causes a change in configuration that renders the 5'→3' exonuclease site inactive.

56. The kit of claim 53 where the ratio of the first polymerase to the second polymerase in the mixture is 1:32 to 1:24.

57. The kit of claim 16, further comprising instructions for allelic discrimination of a target nucleic acid using the mixture and for annealing the probe to a portion of the target nucleic acid.

58. The kit of claim 47, further comprising instructions for allelic discrimination of a target nucleic acid using the mixture.

59. The kit of claim 53, further comprising instructions for allelic discrimination of a target nucleic acid using the mixture.

* * * * *

SEQUENCE LISTING

```
<160> NUMBER OF SEQ ID NOS: 7

<210> SEQ ID NO 1
<211> LENGTH: 28
<212> TYPE: DNA
<213> ORGANISM: Artificial Sequence
<220> FEATURE:
<223> OTHER INFORMATION: oligonucleotide

<400> SEQUENCE: 1
tgggaacttg cagacggaac acacaaac                                    28

<210> SEQ ID NO 2
<211> LENGTH: 28
<212> TYPE: DNA
<213> ORGANISM: Artificial Sequence
<220> FEATURE:
<223> OTHER INFORMATION: oligonucleotide

<400> SEQUENCE: 2
tgggaacttg cagatggaac acacaaac                                    28
```

```
<210> SEQ ID NO 3
<211> LENGTH: 29
<212> TYPE: DNA
<213> ORGANISM: Artificial Sequence
<220> FEATURE:
<223> OTHER INFORMATION: oligonucleotide

<400> SEQUENCE: 3
ttgatggact gcactgcttc atgtgctac                                29

<210> SEQ ID NO 4
<211> LENGTH: 29
<212> TYPE: DNA
<213> ORGANISM: Artificial Sequence
<220> FEATURE:
<223> OTHER INFORMATION: oligonucleotide

<400> SEQUENCE: 4
ttgatggact gcgctgcttc atgtgctac                                29

<210> SEQ ID NO 5
<211> LENGTH: 30
<212> TYPE: DNA
<213> ORGANISM: Artificial Sequence
<220> FEATURE:
<223> OTHER INFORMATION: oligonucleotide

<400> SEQUENCE: 5
caggttgagt gatttatgca gacatttggt                               30

<210> SEQ ID NO 6
<211> LENGTH: 30
<212> TYPE: DNA
<213> ORGANISM: Artificial Sequence
<220> FEATURE:
<223> OTHER INFORMATION: oligonucletide

<400> SEQUENCE: 6
caggttgagt gatttacgca gacatttggt                               30

<210> SEQ ID NO 7
<211> LENGTH: 4
<212> TYPE: PRT
<213> ORGANISM: Artificial Sequence
<220> FEATURE:
<223> OTHER INFORMATION: Conserved Domain
<220> FEATURE:
<221> NAME/KEY: MISC_FEATURE
<222> LOCATION: (2)..(2)
<223> OTHER INFORMATION: Xaa is V or T

<400> SEQUENCE: 7

Ala Xaa Tyr Gly
1
```